US010061888B2

(12) United States Patent
Wang et al.

(10) Patent No.: US 10,061,888 B2
(45) Date of Patent: Aug. 28, 2018

(54) SYSTEM AND METHOD FOR SELECTING A RESPIRATOR

(71) Applicant: Honeywell International Inc., Morris Plains, NJ (US)

(72) Inventors: Xiaoli Wang, Beijing (CN); Henry Chen, Beijing (CN); Hao Bai, Beijing (CN); Paul Derby, Lubbock, TX (US); Hari Thiruvengada, Plymouth, MN (US); Vicken Sarkissian, Irvine, CA (US); Yajun-Edwin Zhang, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 280 days.

(21) Appl. No.: 14/945,822

(22) Filed: Nov. 19, 2015

(65) Prior Publication Data
US 2016/0070851 A1 Mar. 10, 2016

Related U.S. Application Data

(62) Division of application No. 13/839,186, filed on Mar. 15, 2013, now abandoned.

(51) Int. Cl.
*G01N 33/48* (2006.01)
*G01N 33/50* (2006.01)
(Continued)

(52) U.S. Cl.
CPC .......... *G06F 19/12* (2013.01); *G06F 17/5009* (2013.01); *A62B 18/02* (2013.01)

(58) Field of Classification Search
None
See application file for complete search history.

(56) References Cited

U.S. PATENT DOCUMENTS 7,827,038 B2 * 11/2010 Richard ................ A61M 16/06 705/2
9,361,411 B2 * 6/2016 Thiruvengada ..... G06F 17/5009
(Continued)

OTHER PUBLICATIONS

Lei et al. Simulation and evaluation of respirator faceseal leaks using computational fluid dynamics and infrared imaging. Ann. Occup. Hyg., vol. 57, Dec. 13, 2012, pp. 493-506.*

*Primary Examiner* — Russell Scott Negin
(74) *Attorney, Agent, or Firm* — Craige Thompson; Thompson Patent Law

(57) ABSTRACT

Apparatus and associated methods may relate to a system for predicting a respirator fit by comparing a respirator model in a deformed state to a specific facial model. In an illustrative example, an internal measurement may be calculated between an inside part of the respirator model and the facial model. The internal measurement may be compared against a predetermined threshold to determine a fit of the respirator model, for example. In various implementations, the internal measurement may be a distance and/or a volume between the respirator and facial model. In some implementations, a 3D representation of the respirator model may be displayed upon a 3D representation of the facial model. In some implementations, a color-coded facial display may characterize areas of comfort and discomfort with respect to the respirator model. For example, areas of comfort and discomfort may be objectively determined in view of an applied pressure by the respirator.

17 Claims, 15 Drawing Sheets

(51) Int. Cl.
  *G06F 19/12*  (2011.01)
  *G06F 17/50*  (2006.01)
  *A62B 18/02*  (2006.01)

(56) References Cited

U.S. PATENT DOCUMENTS

2006/0023228 A1\* 2/2006 Geng ................... A61B 5/411
                356/601
2006/0048777 A1\* 3/2006 Brookman ............. A62B 7/02
                128/201.22

\* cited by examiner

SYSTEM AND METHOD FOR SELECTING A RESPIRATOR

CROSS-REFERENCE TO RELATED APPLICATIONS

This application is a divisional of U.S. patent application Ser. No. 13/839,186, filed by Wang, et al., on Mar. 15, 2013, entitled "System and Method for Selecting a Respirator." The entire contents of the foregoing application is incorporated herein by reference.

TECHNICAL FIELD

Various embodiments relate generally to personal protective equipment and more specifically to a system and method for predicting an optimal fit of a respirator to a facial area.

BACKGROUND

Personal protective equipment (PPE), such as for example respirators, are widely used in a variety of different applications. For example, many workplaces that subject an employee to hazardous atmospheric conditions require the employee to wear respiratory protection for several hours per day. To be effective, respiratory protection requires a proper seal upon a facial area of the user. A poor seal and thus poor fit may result in leakage and the possibility of the inhalation of contaminants.

Finding a respirator that fits a unique facial area of the user can require the user to try on many different types and sizes of respirators. In some workplace environments, valuable time can be spent attempting to find an optimal fitting respirator. In other workplace environments, an employee may not be able to find a respirator having a suitable fit. For example, the employee may not be given adequate time to try on different respirators, or the employee may not be given an adequate variety of respirator samples to try. Because of the general lack of efficiency and practicality in the prior art there may be a need for a new and improved system and method for predicting an optimal fit of a respirator to a facial area.

SUMMARY

Apparatus and associated methods may relate to a system for predicting a respirator fit by comparing a respirator model in a deformed state to a specific facial model. In an illustrative example, an internal measurement may be calculated between an inside part of the respirator model and the facial model. The internal measurement may be compared against a predetermined threshold to determine a fit of the respirator model, for example. In various implementations, the internal measurement may be a distance and/or a volume between the respirator and facial model. In some implementations, a 3D representation of the respirator model may be displayed upon a 3D representation of the facial model. In some implementations, a color-coded facial display may characterize areas of comfort and discomfort with respect to the respirator model. For example, areas of comfort and discomfort may be objectively determined in view of an applied pressure by the respirator.

In accordance with an exemplary embodiment, an image capture device may generate point cloud data of a body part model and a PPE model. For example, an image capture device may generate point cloud data of a facial area and a respirator. In an exemplary embodiment, point cloud data may be used to overlay a respirator model on a facial model to determine a virtual placement of the respirator model on the facial model. For example, a rigid registration method may be used to align point clouds of the facial model and the respirator model. In some implementations, identifying feature points of the body part model (e.g., nose, mouth) may be correlated with the generated point cloud. In some implementations, a contact line may be determined upon the facial area. Determination of the contact line may provide identification of a portion of a facial area that aligns with the inside part of the respirator.

Various embodiments may achieve one or more advantages. For example, some embodiments may objectively determine whether the hidden, inside part of the respirator will make contact with a portion of the facial area. In accordance with an exemplary embodiment, a predetermined deformation parameter of an outside part (e.g., outside surface) of the respirator may be attributed to a corresponding inside part (e.g., inside surface) of the respirator. The deformation parameter may be determined at each of the vertices or point cloud of the outside and inside parts of the respirator. In an exemplary embodiment, internal measurements may be made between each deformed point cloud or each of the vertices and an aligned part of the facial area to determine a respirator fit.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 3:
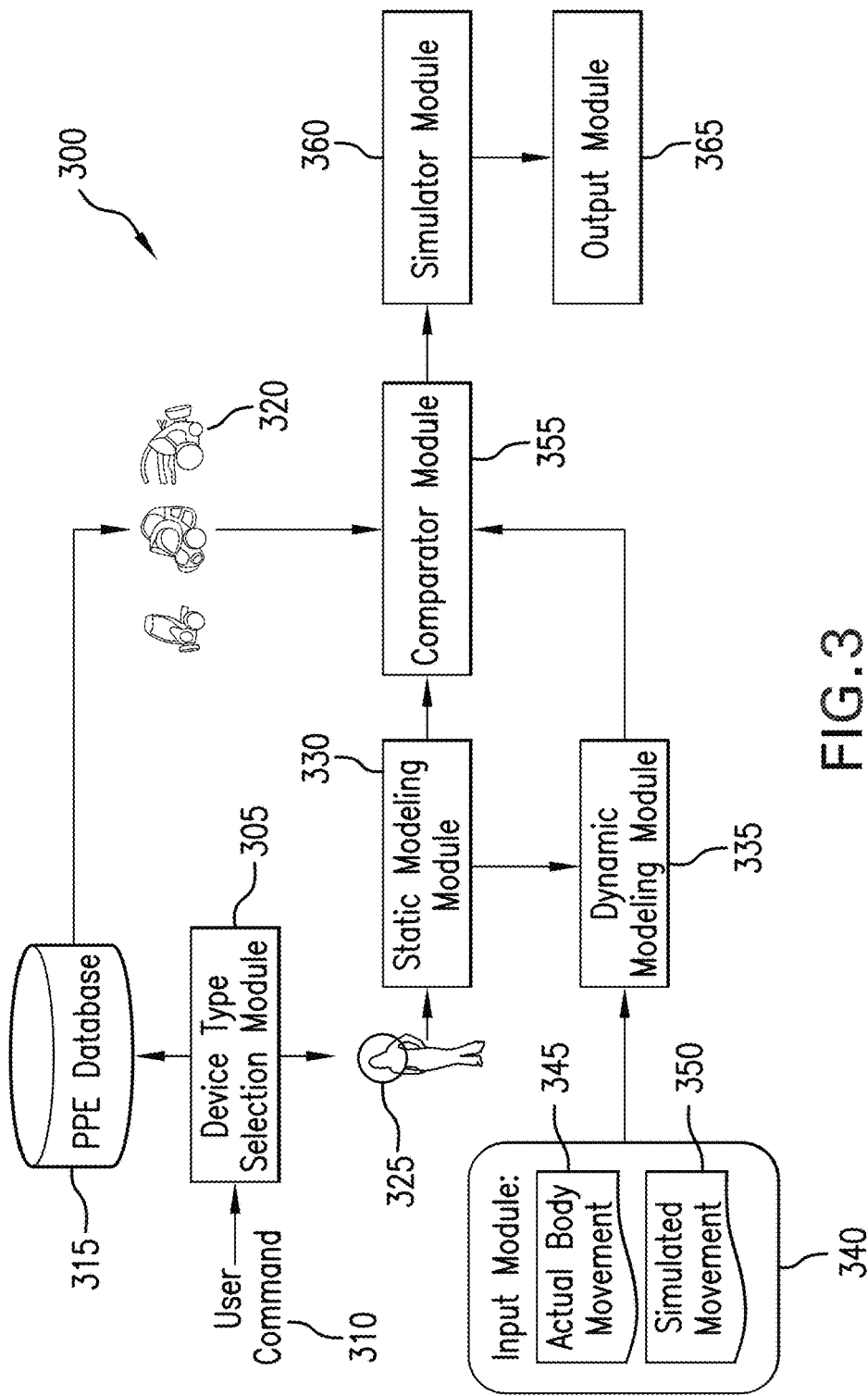
FIG. 3 depicts an overview of an exemplary PPE selection system.
Figure 4:
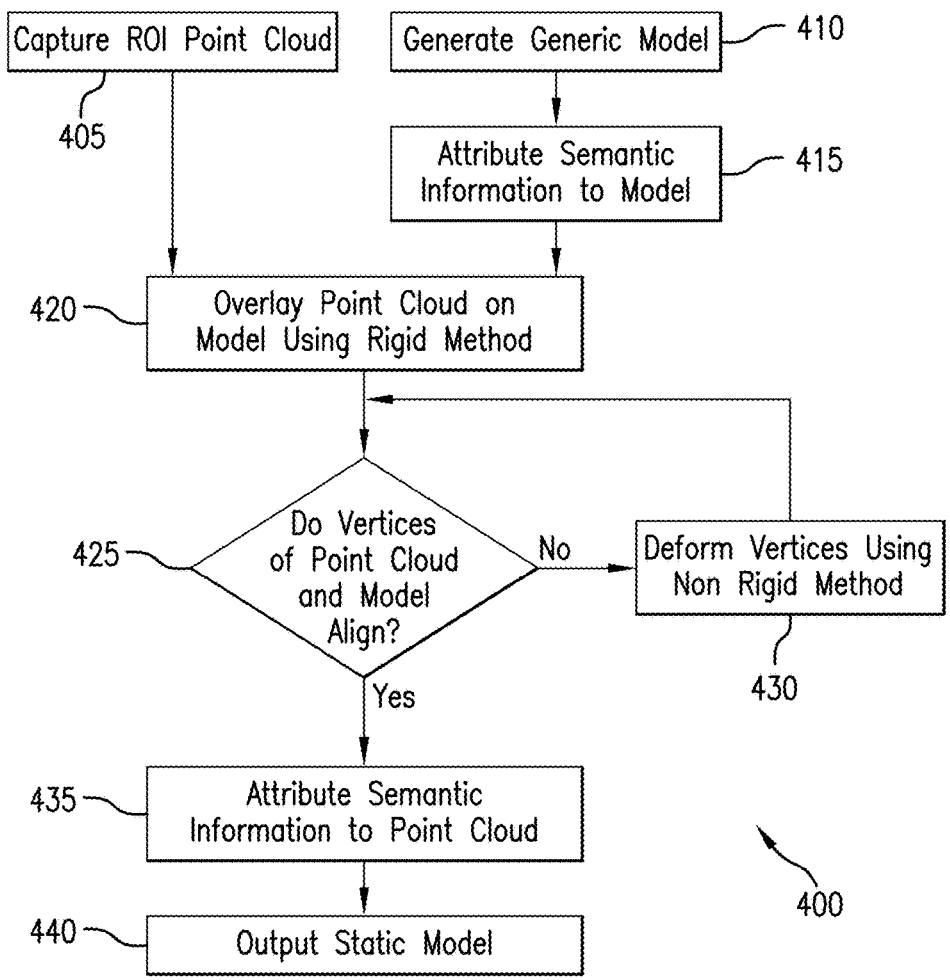
FIG. 4 depicts a flowchart of an exemplary process of a static modeling module.
Figure 5A:
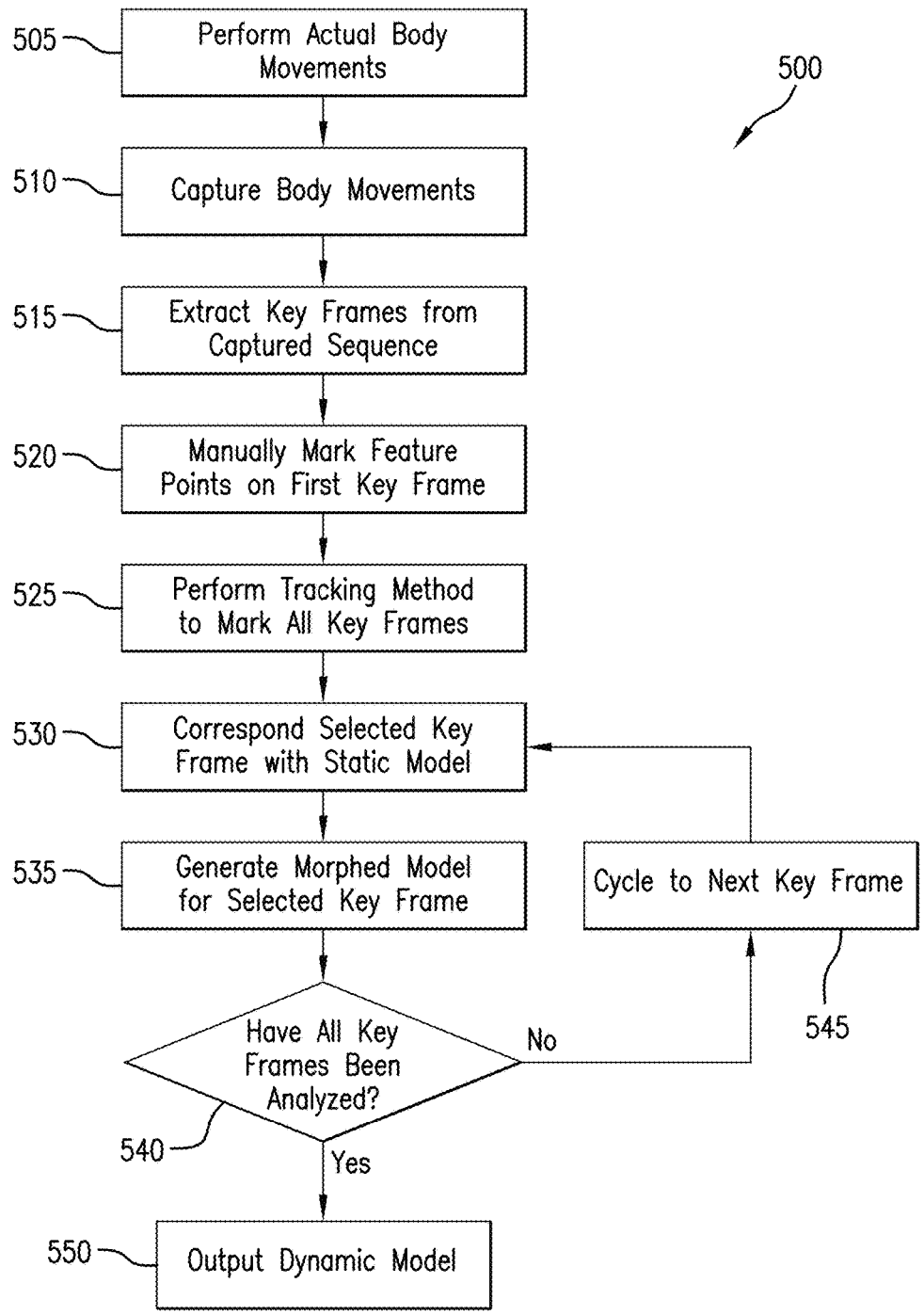
FIG. 5A depicts a flowchart of an exemplary dynamic modeling module using actual body movement.
Figure 5B:
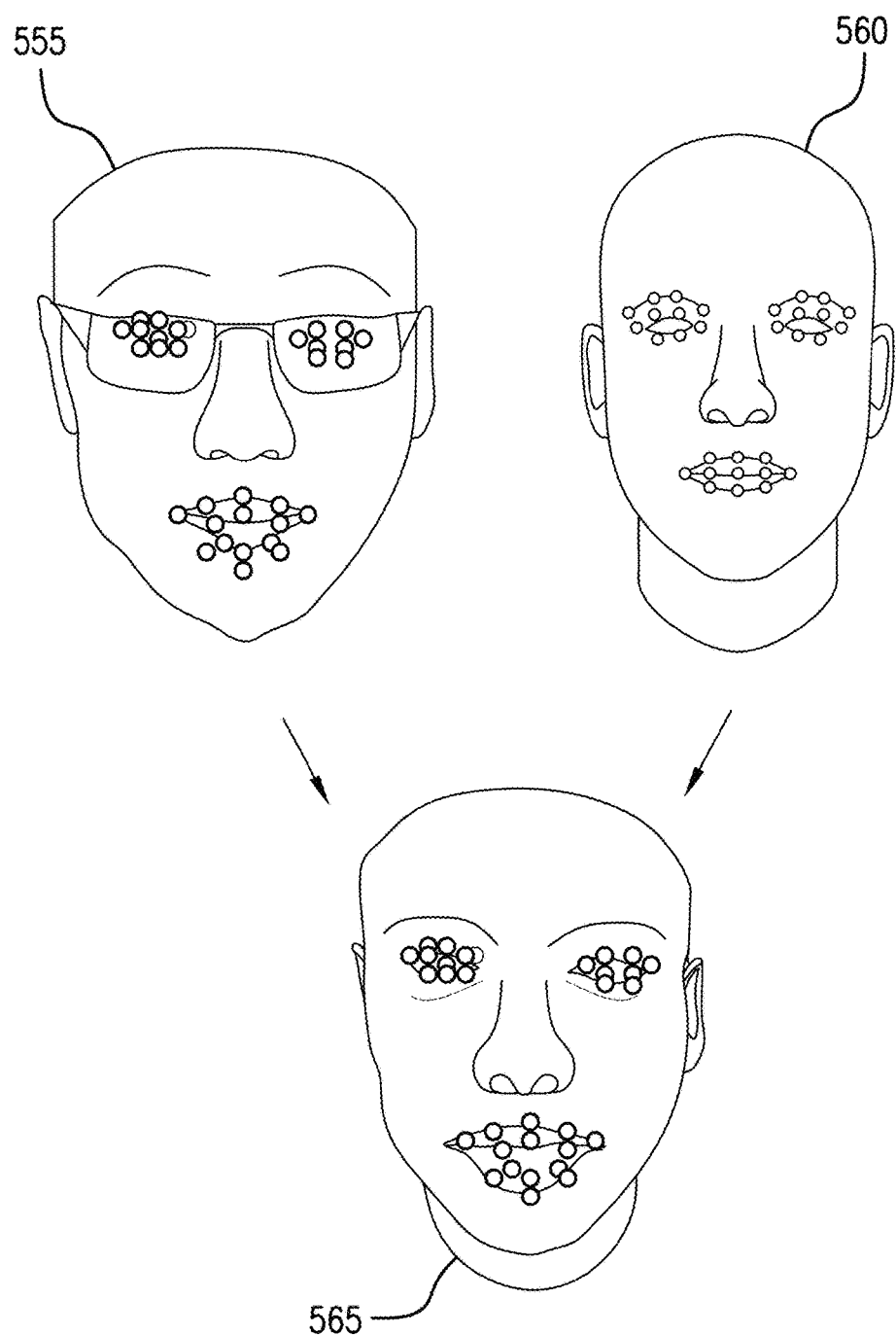
FIG. 5B depicts an exemplary graphical view of the dynamic modeling module of FIG. 5A.

To aid understanding, this document is organized as follows. First, an exemplary PPE selection system for comparing a specific user body part with a respective type of PPE and providing a recommendation and output to a user detailing a fit of the PPE upon the body part is briefly introduced with reference to FIGS. 1-2. Then, with reference to FIGS. 3-6B, the discussion turns to detail an exemplary PPE selection system adapted to evaluate a fit of PPE upon a user based on dynamic conditions. Specifically, FIG. 3 illustrates an exemplary overview of the PPE selection system as detailed in FIGS. 4-6B. FIG. 4 illustrates an exemplary method of obtaining a static model of the user. FIGS. 5a-5b detail an exemplary method of having the user perform actual body movements to obtain a dynamic model, and FIGS. 6a-6b detail an exemplary method of simulating body movements to obtain a dynamic model. Next, FIGS. 7-10 illustrate another exemplary PPE selection system adapted to evaluate a fit of PPE upon a user in both based on an internal space between the PPE and the user body part. Finally, with reference to FIGS. 11-12, an exemplary fit recommendation is illustrated that portrays a fit experience of the PPE upon the user based on color-coding.

Figure 1:
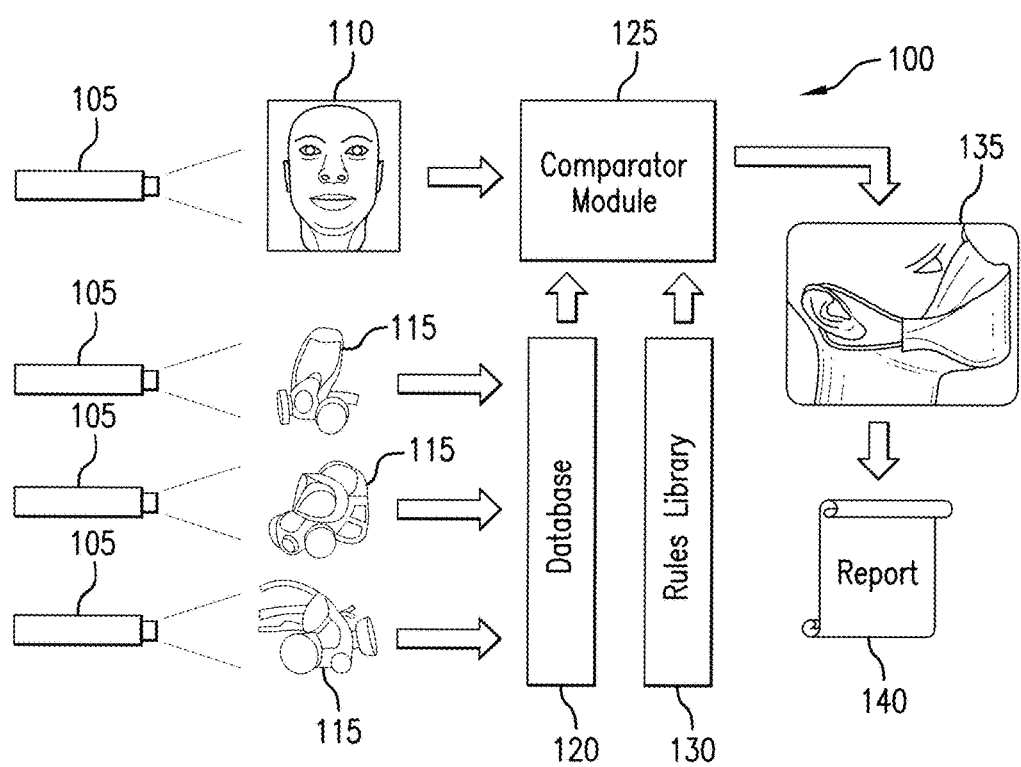
FIG. 1 depicts an overview of an exemplary respirator selection system.

FIG. 1 depicts an overview of an exemplary respirator selection system. A system 100 for selecting a PPE is illustrated, where the system 100 may provide recommendations to a user on which PPE will provide an optimal fit, or provide a best fit among available PPE. A fit level of the PPE upon the user may be determined by a variety of factors determined by the user, employee, and/or manufacturer. For example, an amount of predicted leakage of ambient air through a sealing edge of the respirator may be a determined factor for determining a fit level of the respirator on a facial area of the user. In an exemplary embodiment, if a respirator were to permit a leakage at a rate beyond a predetermined threshold, the respective respirator may be given a low score and/or a non recommendation. In another exemplary embodiment, a force applied by the respirator upon a facial area of the user may be a determinant factor on a recommendation of a particular respirator type of size. If the respirator is predicted to apply pressure to the facial area at a rate or force exceeding a threshold, the respirator may be given a low score and/or a non recommendation because of a possible low comfort level provided to the user by the respirator, for example.

The system 100 may provide fit recommendations or scores based upon captured and analyzed images of the user body part (e.g., facial area) and PPE (e.g., respirator). In the depicted example, the system 100 include one or more image capture devices 105 for capturing representations of a user body part 110 and/or a type of PPE 115. In the depicted example, the user body part 110 is a user facial area. The PPE 115 may be a respirator, for example. In an exemplary embodiment, a series of two-dimensional (2D) images may be captured by the image capture device 105 from which a three-dimensional (3D) image may be assembled. In other exemplary embodiments, a 2D image may be used to determine a PPE fit. In other exemplary embodiments, the image capture device may capture a 3D representation of the body part 110 and/or the PPE 115. In some examples, facial coordinate data representative of a shape of a facial area and respirator coordinate data representative of a respirator shape may be analyzed to provide a fit recommendation. In an exemplary embodiment, the system 100 may load previously captured and/or generated body parts 110 and/or PPE 115.

The system 100 may be used for selecting a variety of PPE 115 to be worn on the intended body part 110. For example, in certain embodiments the system 100 may predictively choose an optimal fitting glove to fit a user hand. In other exemplary embodiments, the system may choose an optimally fitting helmet to fit a head of a user. In an exemplary embodiment, several respirator point cloud data sets each indicative of a specific size and shape respirator 115 may be stored in a database 120. For example, each respirator that an employer offers to employees may be analyzed with associated representative point cloud data, where the representative point cloud data may be stored in a database 120. In an exemplary embodiment, the point cloud data may include x, y, z coordinates which may be assembled to form a 3D image of the intended PPE 115 and/or user body part 110. In an exemplary embodiment, the database 120 may be accessible over a wide-area network (e.g., Internet) to permit a wide selection of PPE 115 to users without the need to personally capture data representative of each eligible PPE 115.

A comparator module 125 compares the PPE 115 with the body part 110 to determine whether the PPE 115 will properly fit the respective body part 110. In an exemplary embodiment, the PPE 115 is overlaid upon the body part 110. For example, a point cloud and/or vertices may be aligned between the PPE 115 and the body part 110. In an exemplary embodiment, the comparator module 125 uses a set of predetermined rules from a rules library 130 to determine whether the PPE 115 properly fits the body part 110. For example, the rules may require the sealing edge of a respirator not to be in contact with the mouth of the user. In another exemplary embodiment, the rules may require the respirator to have a surface area as large as the respirator-receiving portion of the facial area of the user. In another exemplary embodiment, the rules may identify a captured body part, such as for example a facial area, and direct the comparator module to only compare respirators from the database with the body part. In another exemplary embodiment, the rules may identify a captured body part, such as for example a hand, and direct the comparator module to only compare gloves from the database with the body part and not to compare respirators with the captured body part (e.g., hand).

After a fit of the evaluated PPE 115 and body part 110 has been determined, a simulator module 135 may display the fit. For example, the simulator module 135 may display a representation of the respirator worn by the specific facial area of the user. In some examples, a predicted tightness or looseness of the PPE 115 relative the body part 110 may be emphasized in the simulator module 135. For example, a predicted leakage between the sealing edge of the respirator and the facial area may be emphasized. A report 140 may be outputted to the user to assist in providing a recommendation on fit levels of each compared PPE 115. In some examples, a list of evaluated PPE 115 may be included in the report 140 with each of the evaluated PPE 115 having a score or fit level assigned. In some examples, only recommended PPE 115 may be provided in the report 140. In some examples, only the highest scoring three or five PPE 115 may be provided in the report 140.

Figure 2:
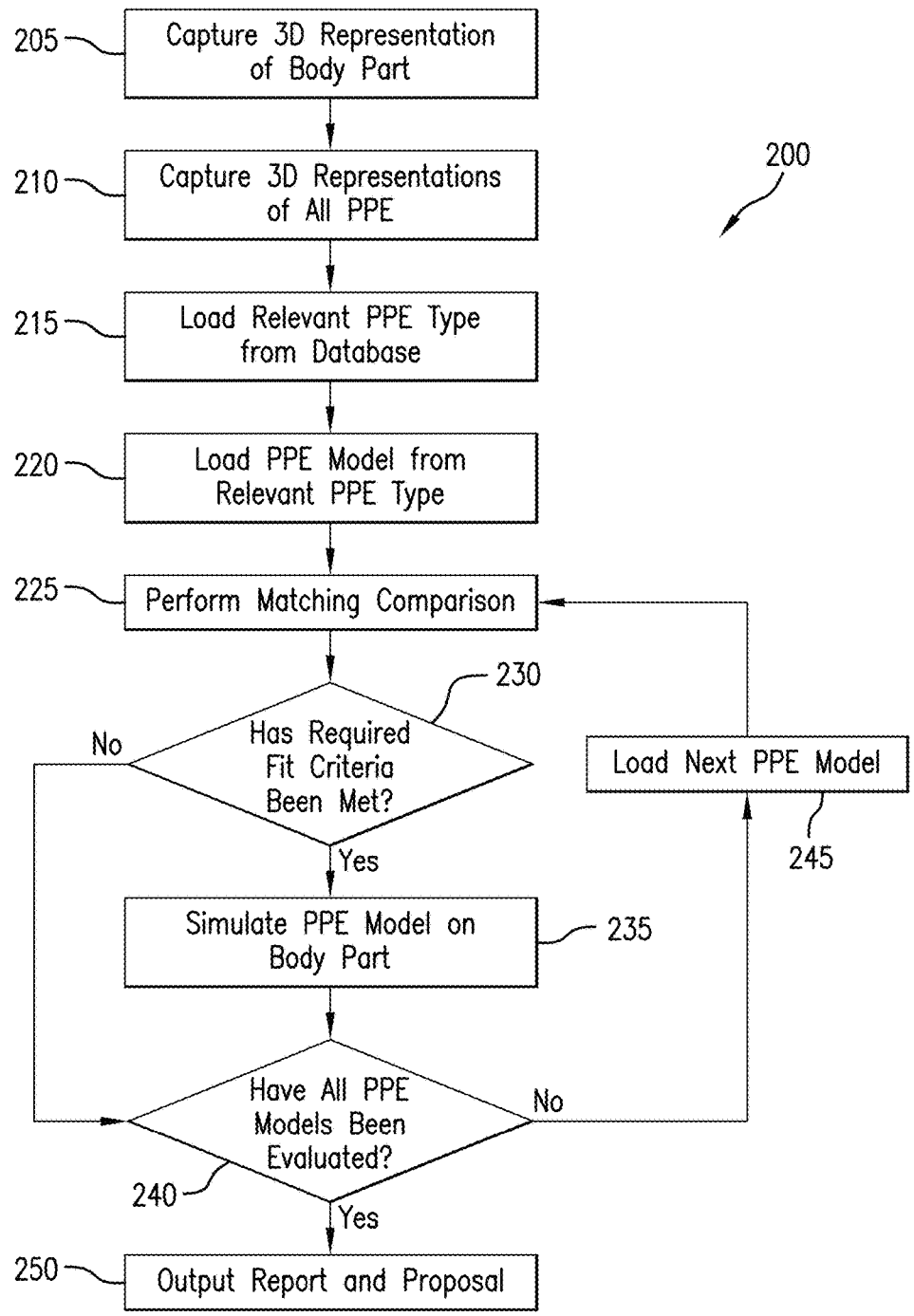
FIG. 2 depicts a flowchart of an exemplary PPE selection system.

FIG. 2 depicts a flowchart of an exemplary PPE selection system. In an exemplary PPE selection system 200, a determination may be made of whether one or more PPE models fit a specific body part. In an exemplary embodiment, the determination may be made by software operated on a processor module. For example, the software may determine which respirator of a plurality of respirator models from a respirator type database fits a specific facial area of a user and output a recommendation to a user.

More specifically, data representing an exemplary body part may be captured as in step 205. In an exemplary embodiment, the data may be captured by an image capture device. For example, an image capture device may scan a body part to build a 3D representation of the body part. In another exemplary embodiment, data representing the body part may be retrieved or computationally loaded. In an exemplary embodiment, the body part data may be retrieved from a body part database having specific body part shapes stored at an earlier date. In other exemplary embodiments, the data representative of a body part may be a generic body part computationally generated or morphed from one or more models. In an exemplary embodiment, the representative body part may be a facial area of a user.

Additionally, data representing one or more types of PPE (e.g., helmets, gloves, PPE) may be captured as in step 210. In an exemplary embodiment, the data may be captured by an image capture device. For example, an image capture device may scan PPE to build a 3D representation of the PPE. In another exemplary embodiment, data representing the PPE may be retrieved or computationally loaded. In an exemplary embodiment, the PPE data may be retrieved from a PPE database having specific PPE shapes stored at an earlier date. In an exemplary embodiment, the representative PPE may be a respirator.

A particular type of PPE (e.g., helmets, gloves, PPE) to be worn over or upon the loaded body part may be retrieved or computationally loaded as in step 215. For example, a PPE type including respirator models may be loaded if the intended body part may be a facial area. In another exemplary embodiment, a PPE type having gloves may be loaded if the intended body part may be a hand.

A first PPE model from the loaded relevant PPE type may be retrieved as in step 220 to be compared via a comparator module with the captured body part as in step 225. Each PPE model may be distinguishable because of a size, shape, or other criteria which may affect the fit of the PPE on the user body part. The comparison may determine whether the PPE model has a shape that will permit an acceptable fit over the shape of the body part. For example, the PPE model may be required to meet or exceed one or more thresholds or rules previously determined as indicative of proper or optimal fitting criteria. In some exemplary embodiments, the PPE model may be required to fit the body part in both static and dynamic states of the body part.

If the PPE model is determined to fit the body part as illustrated in step 230, the PPE model may be simulated on the body part as in step 235. In an exemplary embodiment, the PPE model and body part may be displayed to the user in a 3D representation. In some exemplary embodiments, the user may rotate and pan a 3D representation of the simulated body part and PPE model. In some exemplary embodiments, the simulated representation may provide visual feedback to the user detailing areas of the PPE model that are not predicted or determined to fit the respective body part. For example, one or more colors may be overlaid upon the representation to indicate areas upon the body part that are predicted to be uncomfortable as a result of wearing the PPE model. In other examples, a blinking or flashing area may indicate an area of the PPE model that does not conform to a minimum threshold determined to be required to provide a proper and/or comfortable fit. For example, a portion of a sealing edge of a respirator may blink if a leak is predicted to be present in the respective portion.

After the first PPE model is determined to fit and simulated to the user, the software may determine if there are any other PPE models in the chosen PPE type group that are to be evaluated against the respective body part as illustrated by step 240. If so, the software cycles to a second PPE model as illustrated by step 245 and repeats the process of steps 225-240. If there are no more PPE models from the PPE type group, a report and proposal may be generated for output to the user as illustrated in step 250. In some exemplary embodiments, the report and proposal may include the top three PPE models that have the best fit with respect to the specific body part. In some exemplary embodiments, the top PPE models or all of the PPE models evaluated may be provided with a fit score to the user. In some exemplary embodiments, a different PPE type group may require comparison with the body part, in which case some or all of the process may be repeated.

FIG. 3 depicts an overview of an exemplary PPE selection system. A PPE selection system 300 may be used to select an optimal fit PPE for a user body part during dynamic conditions of the user body part. The PPE selection system 300 includes a device type selection module 305 for receiving a command from a user 310. In an exemplary embodiment, the device type selection module 305 sends commands to a PPE database 315. The PPE database 315 may include a variety of types of PPE 320, such as for example gloves, respirators, and helmets. In an exemplary embodiment, the device type selection module 310 may relay a command 310 indicative of a particular type of PPE 320, such as for example a facial respirator. In an exemplary embodiment, the command 310 may be indicative of a particular user body part 325 to be matched with the PPE 320 from the PPE database 315.

In some exemplary embodiments, the device type selection module 305 may direct an image capture device (not shown) to capture a 2D or 3D image of the selected body part 325. In some embodiments, the PPE 320 may be modeled in a corresponding 3D shape. In some exemplary embodiments, one or more device range rules may define a capture range of the body part 325 for the corresponding PPE 320. For example, with half-mask respirators, the device range rules may define a capture range as the user face. In an exemplary embodiment of multiple PPE candidates, a capture range computing step may calculate a maximum facial area range that may accommodate the PPE and then correlate the range with each PPE to determine whether the respective PPE fits within the facial area range.

Once the user body part is captured or retrieved, such as for example from a database, the user body part may be modeled using a static modeling module 330. The static modeling module generates a 3D model of the user body part to be used by a dynamic modeling module 335. The dynamic modeling module 335 communicates with an input module 340 for generating dynamic models of the user body part 325. In one exemplary embodiment, the input module 340 communicates actual body movement 345 to the dynamic modeling module 335 for generating a dynamic model using actual movement from the user. In another exemplary embodiment, the input module 340 communicates simulated movement 350 to the dynamic modeling module 335 to generate a dynamic model based upon a simulated body part movement.

By using a dynamic model, a more realistic fit may be realized between the user body part and the PPE, since a user generally undergoes some movement while wearing the PPE. The dynamic model may then be compared with the PPE models 320 from the PPE database 315 by a comparator module 355. The comparator module 355 may determine a fit level of the PPE model 320 with the dynamic model from the dynamic modeling module 335 based on a variety of predetermined criteria or rules. For example, the comparator module 355 may evaluate a size of the PPE model 320 with the dynamic model in an extreme position (e.g., open mouth) to determine whether the PPE (e.g., respirator) will fit the user body part (e.g., facial area) in the extreme position. The calculated results of the comparator module 355 may be summarized for output and visualization.

In an exemplary embodiment, the comparator module 355 may fit the PPE model candidate 320 to the dynamic model set according to mapping rules. The comparator module 355 may then calculate the difference between the PPE model candidate 320 and dynamic model outputted from the dynamic modeling module 335. According to a set of predetermined evaluation rules, a fit score of each PPE model 320 may be provided relative the dynamic model. Lastly, the comparator module 355 may output an optimal fit PPE 320 based on simulated comfort and fit. In an exemplary embodiment, a respective fit of the PPE 320 may be visualized by color coding for user.

In an exemplary embodiment, the result from the comparator module 355 may be outputted to a simulator module 360 for display to a user through an output module. In an exemplary embodiment, the simulator module may graphically overlay the 3D PPE model 320 upon a 3D representation of the user body part 325 to illustrate to the user the PPE model 320 being virtually worn on the user body part 325. In some exemplary embodiments, a fit level, score, or color may accompany the graphical illustration for ease in interpreting the results.

In an exemplary embodiment, the output module 365 may comprise a display module. In some exemplary embodiments, the output module 365 may comprise a printed report. In some exemplary embodiments, the report may provide 3D visual representations of the PPE virtually worn by the user. In some exemplary embodiments, the report may provide a detailed list of a fit level or score of each evaluated PPE with respect to a region of interest of the user. In some exemplary embodiments, the report may provide a color-coded graphical representation of a PPE virtual fit on the user. In some exemplary embodiments the color-coded graphical representation may illustrate, through color-coding, different levels of pressure as applied to the user by the PPE when virtually worn.

FIG. 4 depicts a flowchart of an exemplary process of a static modeling module. A static modeling module 400 may be used to generate an objective static 3D model of a body part. The static model may be used in dynamic modeling processes. In some exemplary embodiments, the PPE may be compared directly to the static model if dynamic comparison is not necessary. In an exemplary embodiment, a static model of a facial area may be generated with the static modeling module 400. In some exemplary embodiments, the generated static model may be in 2D form.

When generating the static model, the module 400 first captures a region of interest (ROI) point cloud of a user as in step 405. The ROI may be the portion of the body that corresponds to the evaluated PPE. For example, when evaluating respirator fit, the ROI may be a facial area of the user. In an exemplary embodiment, the point cloud may include x, y, z coordinates assembled to form a 3D image of the respective body part.

A generic model may also generated as illustrated in step 410 to generically match the body portion captured by the point cloud as in step 405. For example, if a facial area is the ROI, the generic model may be representative of a generic user face. In exemplary embodiments, the generic model may be retrieved from a database of generic models. In some exemplary embodiments, a preliminary screening process may be completed to find a generic model being close in shape to the captured ROI. Predetermined semantic information is attributed to the generic model as in step 415. The semantic information may be distinguishable body feature points of the corresponding body part. For example, a facial area may include semantic information associated with the eyes, ears, mouth corners, and a nose tip. The semantic information may be attributed to the vertices of the generic model, for example. In an exemplary embodiment, a set of rules which define the semantic information may include MPEG4 format definition rules.

The point cloud of the ROI is then overlaid on the generic face model by a rigid method as in step 420. In an exemplary embodiment, the rigid method may include a rigid registration or alignment of vertices of the ROI and vertices of the generic model. In an exemplary embodiment, the aligned vertices may correspond to proximally similar or equivalent locations on the modeled body part. For example, the nose portion of the point cloud of the ROI may be aligned with nose portion of the generic model.

The module 400 then determines whether the vertices of the point cloud align or match to an acceptable level or threshold as illustrated in step 425. For example, if the vertices of the point cloud do not exactly align as determined by a predetermined threshold, the vertices of the point cloud and the generic model are deemed not to align to an acceptable level. If the vertices do not align to an acceptable level, the vertices of the generic model may be deformed to fit the overlaid point cloud by a non-rigid registration method. In an exemplary embodiment, a non-rigid registration method may include blending the non-aligning vertices of the generic model with neighboring vertices. In another exemplary embodiment, certain vertices of the generic model may be moved a predetermined allowable distance to reach an alignment with the point cloud of the ROI.

Once alignment is reached with the vertices of the point cloud and vertices of the generic model, the semantic information of each vertex on the generic face model may be attributed to the point cloud. For example, the vertices of the point cloud may receive the semantic information and be stored within the properties of the point cloud such that each of the points in the point cloud may include identification properties corresponding to a location of the point in the point cloud. For example a point of the point cloud located at a position corresponding to a nose tip may include semantic information identifying the point as "nose tip". The static model having the point cloud with semantic information may then be outputted as in step 440. In an exemplary embodiment, the static model may be outputted to the dynamic modeling module. In another exemplary embodiment, the static model may be outputted to a comparator module. In yet another exemplary embodiment, the static model may be outputted to a simulator module. In an exemplary embodiment, the static model may be a 3D representation.

FIG. 5A depicts a flowchart of an exemplary dynamic modeling module using actual body movement. A dynamic modeling module 500 uses actual body movement to generate a dynamic model as described with reference to FIG. 3. In an exemplary embodiment, the dynamic model may be generated in 3D form. In the depicted example, a user performs actual body movement as in step 505 and an image capture device captures the body movement as in step 510. In some exemplary embodiments, the body movement performed may correlate with body movement commonly performed while wearing associated PPE. For example, the user may speak a variety of phrases when fitting a user with a respirator since it may be common for a user to speak or move their mouth while wearing the respirator.

Once a series of movements are captured, such as for example by video or a plurality of images, a key frame may be extracted from the captured sequence as in step 515. The key frame may be an image reflecting a particular user movement, for example. In an exemplary embodiment, the key frame may simply be a generic reference or starting image. In an exemplary embodiment, the user may then manually mark feature points on the selected, first key frame as in step 520. The feature points may correspond with distinguishable features on the body part captured. For example, a nose or mouth may be feature points for a captured facial area. In some exemplary embodiments, the user manually selects the feature points by visually selecting the feature points on a computer display. In some exemplary embodiments, the user manually selects the feature points by selecting body coordinates predetermined to be associated with the respective feature point. In some exemplary embodiments, the selection of the feature points may be automated via an image recognition software or device. In some exemplary embodiments, the feature points may be appointed identifying information, such as for example semantic information.

Once the feature points of the first key frame are identified and selected, a tracking method may be performed to identify and mark feature points on all key frames based on the selected feature points of the first key frame as in step 525. In an exemplary embodiment, the tracking method may track the feature points via proximity of similar vertices in neighboring key frames. In some exemplary embodiments, the tracking method may be automatically performed by the dynamic module 500.

One of the key frames having feature points may then be selected and the feature points corresponded to a static 3D model as in step 530. In an exemplary embodiment, the static 3D model may be generated according to the detailed process exemplified in FIG. 4. The feature points may be linked to similarly located points from the point cloud of the static model such that properties of the points from the point cloud of the static model may be transferred to the feature points of the key frame, for example.

In an exemplary embodiment, a morphed model may then be generated by morphing the static model to a facial position of the key frame. For example, the point cloud of the static model may be altered to a proximal location of the feature points. If the key frame illustrates a user having an open mouth, the static model and associated point cloud may be altered to reflect an open mouth morphed static model. In an exemplary embodiment, the morphable model may be generated by performing rigid and/or non-rigid registration methods with vertices or points between the key frame and the static model.

In step 540, the module 500 determines whether there are additional key frames to analyze. If there are more key frames to analyze, then the module cycles to the next key frame as in step 545 and returns to step 530. If there are no more key frames to analyze, then a dynamic model may be outputted as in step 550. In an exemplary embodiment, the dynamic model may be outputted to a comparator module for comparing the PPE model with the dynamic model to determine whether the PPE model fits the dynamic model. In an exemplary embodiment, the dynamic model may be outputted as a 3D model set for all captured key frames.

FIG. 5B depicts an exemplary graphical view of the dynamic modeling module of FIG. 5A. As illustrated, a key frame 555 having feature points manually marked on the key frame as described with reference to step 520 of FIG. 5A. The static model 560 may be generated by the static modeling module as described with reference to FIG. 4. As exemplified the point cloud of the static model may be located along similar facial features as the feature points of the key frame. A morphable model 565 may be generated by combining the key frame and the static model as described with reference to step 535 of FIG. 5A.

Figure 6A:
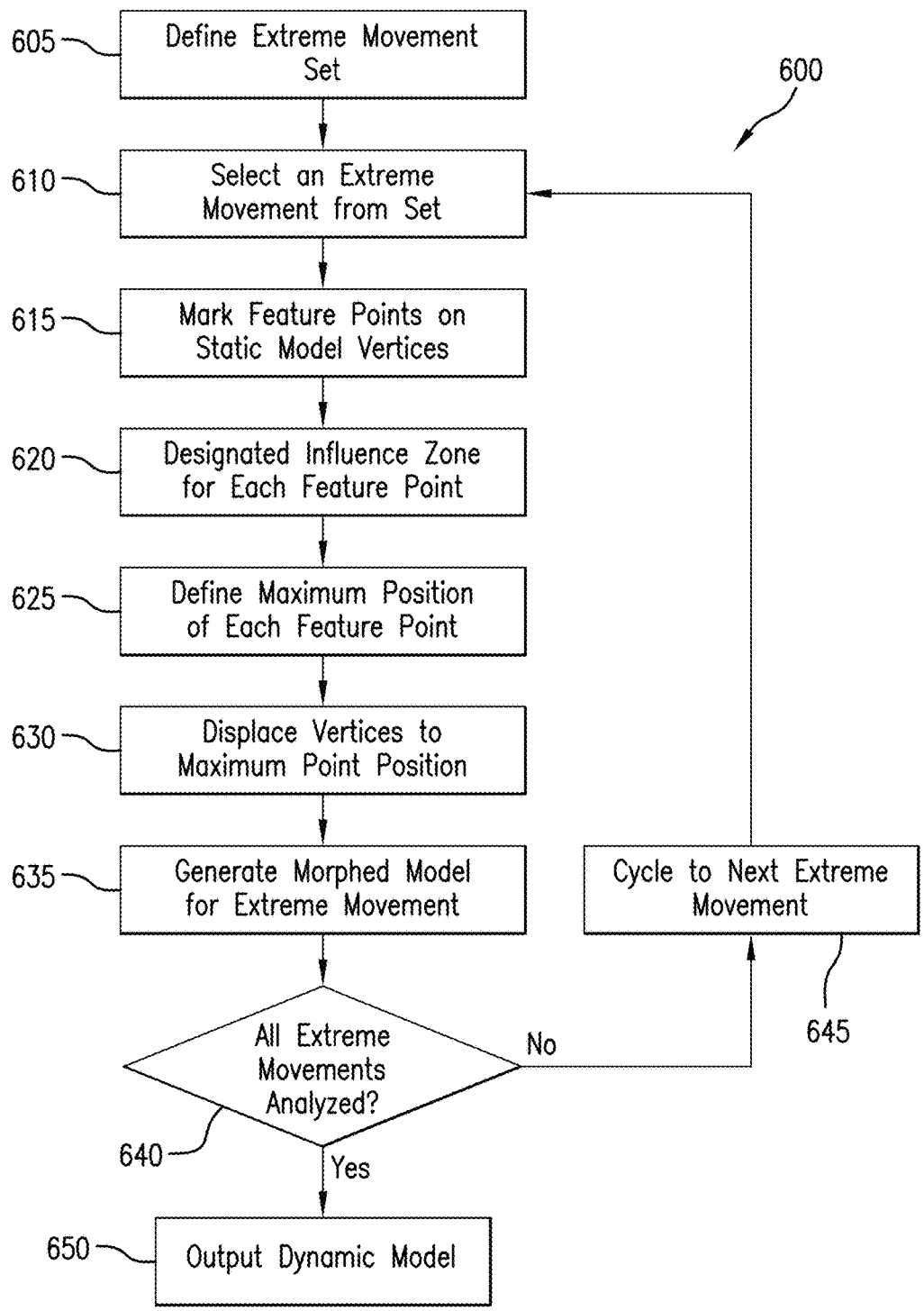
FIG. 6A depicts a flowchart of an exemplary dynamic modeling module using simulated body movement.

FIG. 6A depicts a flowchart of an exemplary dynamic modeling module using simulated body movement. A dynamic modeling module 600 uses simulated body movement to generate a dynamic model as described with reference to FIG. 3. In an exemplary embodiment, the dynamic model may be generated in 3D form. In an exemplary embodiment, an extreme movement set is defined as in step 605. The extreme movement set may be defined by a user in an exemplary embodiment. In other exemplary embodiments, the extreme movement set may be defined by the PPE manufacturer, regulatory agency, and/or employer. In an exemplary embodiment of a respirator, extreme movements may include raising the head, bowing the head, speaking, and/or opening the mouth. In an exemplary embodiment, the extreme movement set may be defined according to actions a user may typically undergo while wearing the respective PPE.

Once the extreme movement set is defined, a first extreme movement may be selected from the set as in step 610. Feature points affected by the selected extreme movement are marked or identified on a static model. For example, if the extreme movement selected mimics an open mouth, feature points surrounding a mouth of the static model may be marked or identified. In an exemplary embodiment, the feature points are linked to corresponding proximal vertices. The static model may be generated by a process as exemplified with reference to FIG. 4, for example.

An influence zone of each feature point may also be defined on the static model as illustrated by step 620. In an exemplary embodiment, the influence zone may be a proximal area of each feature point that may be affected by movement of the respective vertex. In an exemplary embodiment, the feature points and/or feature point influence area may correspond to predetermined data points of an MPEG 4 standard. In an exemplary embodiment, the feature points may include semantic information.

In some exemplary embodiments, the user manually selects the feature points by selecting body coordinates predetermined to be associated with the respective feature point. In some exemplary embodiments, the selection of the feature points may be automated via an image recognition software or device. In some exemplary embodiments, the feature points may be appointed identifying information, such as for example semantic information.

The maximum feature point position is also defined as in step 625. The maximum feature point may correspond to a maximum distance and x, y, z coordinate location of the feature point away from a normal or current location of the feature point on the static model. The vertices and linked feature points are then displaced to the maximum position as defined by the extreme movement as in step 630 and a morphed model is formed as in step 635. Under a prior defined deformation function affect, neighbor related points on static model are displaced to a new position. In an exemplary embodiment, the displacement position of neighbor points can be calculated by:

$$D_{vertex}=D_{FP}*H(vertex,FP)$$

Where $D_{vertex}$ may be the displacement position of neighbors, $D_{FP}$ is displacement of feature points, H is the deformation function. The influence zone of each feature point may also be blended or altered according to linked feature point movement. In an exemplary embodiment, if a vertex is affected by more than one feature point, neighboring vertices may be blended by a weighted sum.

A deformation function may be defined as:

$$H(f) = \begin{cases} T & |f| \le \frac{1-\beta}{2T} \\ \frac{T}{2}\left[1+\cos\left(\frac{\pi T}{\beta}\left[|f|-\frac{1-\beta}{2T}\right]\right)\right], & \frac{1-\beta}{2T} < |f| \le \frac{1+\beta}{2T} \\ 0 & \text{otherwise} \end{cases}$$

where T is the radius of the area that applies the deformation, and β with the scope of (0, 1) is a parameter to adjust the deformation degree; if β is close to 1, the deformation will be smooth, and if β is close to 0, the deformation will be sharp.

In step 640, the module 600 determines whether there are additional key frames to analyze. If there are more extreme movements to analyze, the module cycles to the next extreme movement as in step 645 and returns to step 610. If there are no more extreme movements to analyze, a dynamic model may be outputted as in step 650. In an exemplary embodiment, the dynamic model may be outputted to a comparator module for comparing the PPE model with the dynamic model to determine whether the PPE model fits the dynamic model. In an exemplary embodiment, the dynamic model may be outputted as a 3D model set for all captured key frames.

Figure 6B:
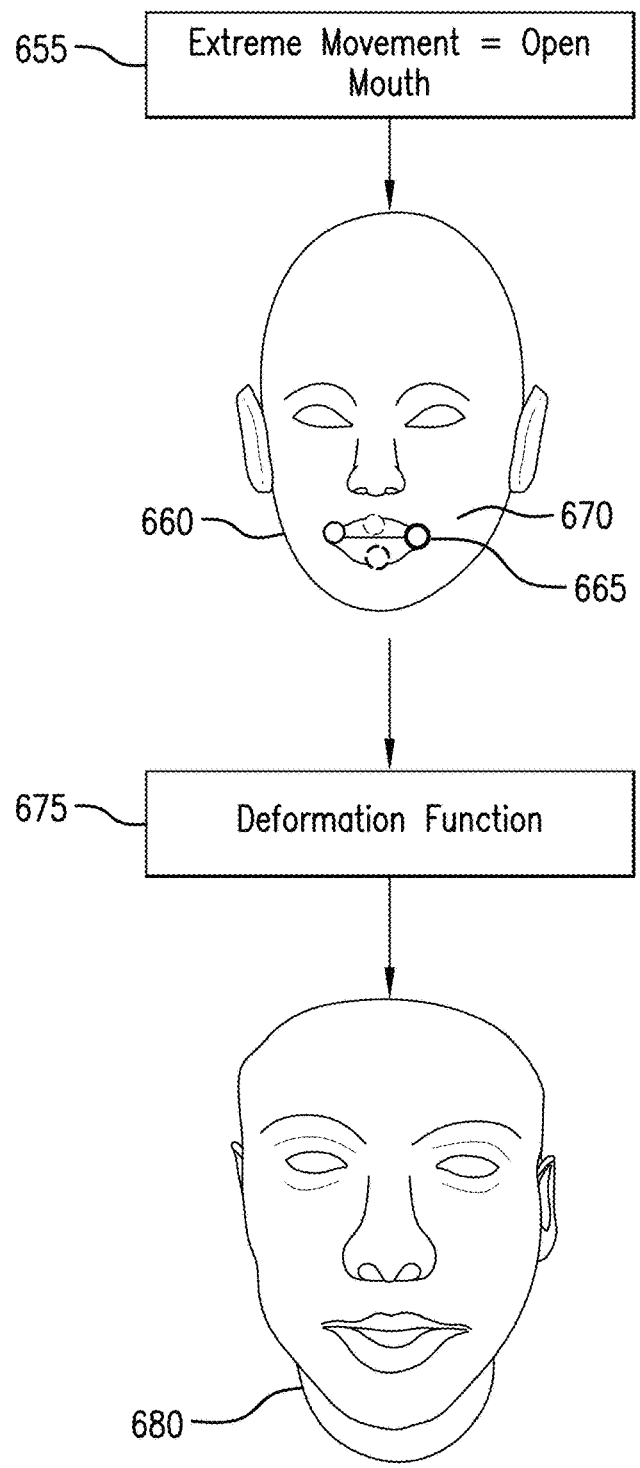
FIG. 6B depicts a graphical view of the exemplary dynamic modeling module of FIG. 6A.

FIG. 6B depicts a graphical view of the exemplary dynamic modeling module of FIG. 6A. The exemplary process includes a first defined extreme movement 655, such as for example an open mouth. A static model 660 may be imported, such as for example the static model generated by the static model module with reference to FIG. 4. The feature points 665 and influence zones 670 corresponding to the extreme movement 655 are marked on the static model 660. In an exemplary embodiment, the feature points may be located by correspondence with an MPEG 4 standard. A deformation function 675 may be executed to morph the static model by displacing the feature points and influence zone according to the maximum position as defined by the extreme movement. Then, a morphed dynamic model 680 is outputted. The dynamic model may be generated in 3D form. In an exemplary embodiment, the dynamic model has a body position correlating to the defined extreme movement.

Figure 7:
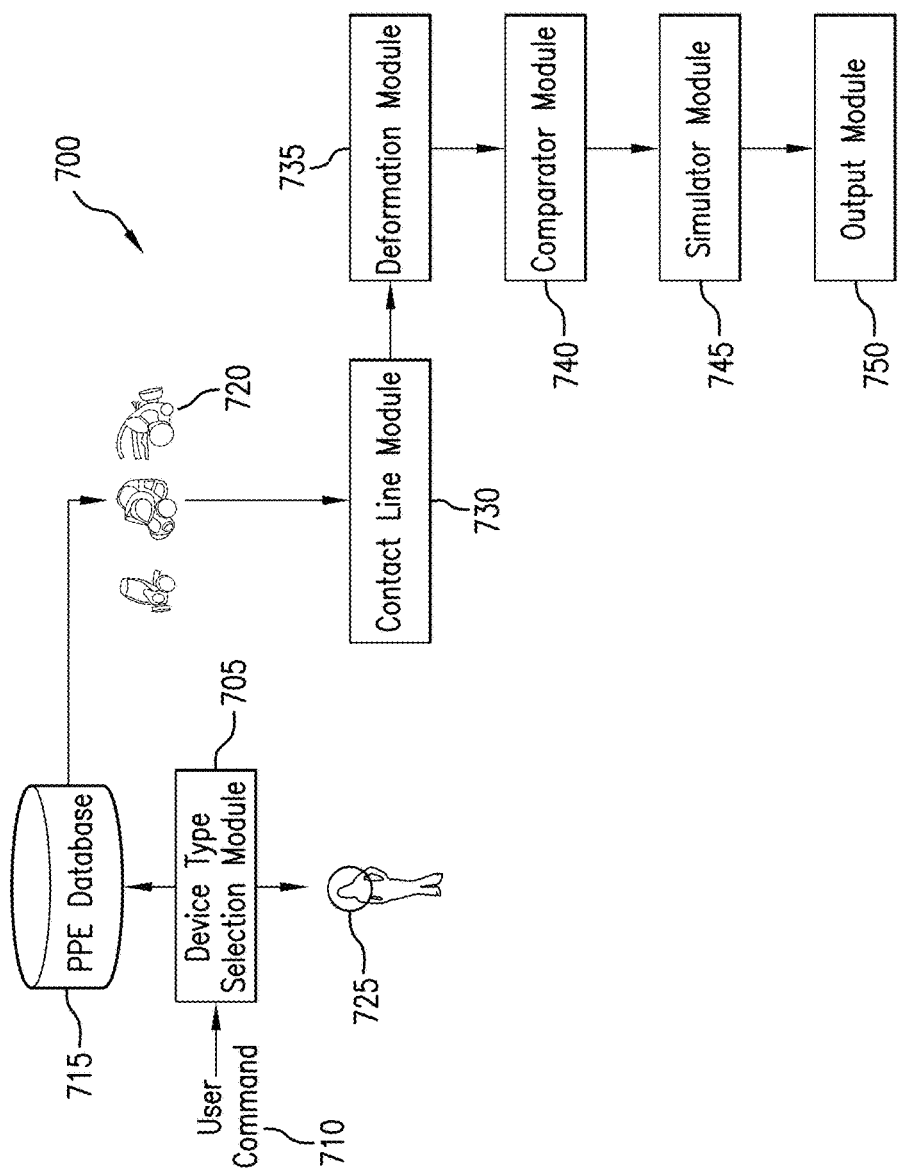
FIG. 7 depicts an overview of another exemplary PPE selection system.

FIG. 7 depicts an overview of another exemplary PPE selection system. A PPE selection system 700 may be used to select an optimal fit PPE for a user body part based on an internal space measured between the PPE and the body part. In an exemplary embodiment, the internal space may be measured during a deformed state of the PPE. The PPE selection system 700 includes a device type selection module 705 for receiving a command from a user 710. In the depicted example, the device type selection module 705 sends commands to a PPE database 715. The PPE database 715 may include a variety of types of PPE 720, such as for example gloves, respirators, and helmets. In an exemplary embodiment, the device type selection module 710 may relay a command 710 indicative of a particular type of PPE 720, such as for example a facial respirator. In an exemplary embodiment, the command 710 may be indicative of a particular user body part 725 to be matched with the PPE 720 from the PPE database 715.

In some exemplary embodiments, the device type selection module 705 may direct an image capture device (not shown) to capture a 2D or 3D image of the selected body part 725. In some embodiments, the PPE 720 may be modeled in a corresponding 3D shape. In some exemplary embodiments, one or more device range rules may define a capture range of the body part 725 for the corresponding PPE 720. For example, with half-mask respirators, the device range rules may define a capture range as the user face. In an exemplary embodiment of multiple PPE candidates 720, a capture range computing step may calculate a maximum facial area range that may accommodate the PPE 720 and then correlate the range with each PPE 720 to determine whether the respective PPE 720 fits within the facial area range.

Once the user body part 725 is captured or retrieved, such as for example from a database, the user body part 725 may be modeled using a contact line module 730. The contact line module 730 determines a contact line of the edge of the PPE 720 on the body part 725 of the user. For example, a respirator sealing edge may be defined as the contact line since the sealing edge may be the primary portion of the respirator that makes contact with the user facial area. The contact line may be determined by capturing an image of the user wearing the PPE 720 and not wearing the PPE 720, and then using a subtractive function to find the contact line. In an exemplary embodiment, the contact line may be found by capturing a 2D or 3D image of the user wearing and not wearing the PPE 720. In another exemplary embodiment, the contact line may be determined using previously captured models of users and/or PPE 720. For example, the previously captured models may be aligned using a rigid or non-rigid registration method to calculate a contact line. Once the contact line is found or calculated, the portion of the body part 725 confined by the contact line may be determined. For example, a portion of a face confined and within the contact line of a respirator may include a portion of a nose and a mouth.

A deformation module 735 may then be used to deform the PPE 720. The PPE 720 may be deformed according to a set of predetermined rules. For example, if a respirator is known to partially collapse inwards a certain percentage during wear, the PPE 720 model may be deformed an amount or distance equivalent to a calculated standard collapse of an in-use respirator. In another exemplary embodiment, the degree of deformation may be determined by a maximum flex permissible by the construction of the PPE 720. In an exemplary embodiment, a deformation of an inside surface or part of the PPE 720 may be determined or calculated from a deformation of an outside surface or part of the PPE 720. In another exemplary embodiment, a deformation of an outside part of the PPE 720 may be computed by comparing the outside part of the PPE 720 to a deformation of the inside part of the PPE 720.

A comparator module 755 may determine a fit level of the deformed PPE 720 model 720 with respect to the portion of the body part 725 internal or confined by the contact line. In comparison, an internal measurement may be made between the internal surface of the PPE 720 and the portion of the body part 725 confined or internal to the contact line. For example, a distance between an inside surface of a respirator and a portion of a user face perpendicular to the inside surface may be calculated while the respirator is in the deformed state. In an exemplary embodiment, the internal measurement may be a distance between the PPE 720 and the body part 725. In another exemplary embodiment, the internal measurement may be an internal volume confined between the inside of the PPE 720 and the corresponding body part 725. In some exemplary embodiments, the internal measurement may be compared against a predetermined threshold to determine whether the PPE 720 meets predetermined fit criteria. For example, if the predetermined threshold is not large enough, the PPE 720 may be disqualified from an acceptable fit category of PPE 720. The calculated results of the comparator module 740 may be summarized for output and visualization.

In an exemplary embodiment, the internal measurement may use an implicit function to calculate a distance between the inside part of the PPE 720 and the corresponding body part 725. A Gaussian smooth function may then be applied to the distance calculation, for example. In some exemplary embodiments, a color-coded result of the internal measurement may be outputted to a user.

In an exemplary embodiment, the comparator module 740 may fit the PPE 720 model candidate 720 to the user body part 725 set according to mapping rules. According to a set of predetermined evaluation rules, a fit score of each PPE 720 model 720 may be provided relative the user body part 725. Lastly, the comparator module 740 may output an optimal fit PPE 720 based on simulated comfort and fit. In an exemplary embodiment, a respective fit of the PPE 720 may be visualized by color coding for user.

In an exemplary embodiment, the result from the comparator module 740 may be outputted to a simulator module 745 for display to a user through an output module. In an exemplary embodiment, the simulator module may graphically overlay the 3D PPE 720 model 720 upon a 3D representation of the user body part 725 to illustrate to the user the PPE 720 model 720 being virtually worn on the user body part 725. In some exemplary embodiments, a fit level, score, or color may accompany the graphical illustration for ease in interpreting the results.

In an exemplary embodiment, the output module 750 may comprise a display module. In some exemplary embodiments, the output module 750 may comprise a printed report. In some exemplary embodiments, the report may provide 3D visual representations of the PPE 720 device virtually worn by the user. In some exemplary embodiments, the report may provide a detailed list of a fit level or score of each evaluated PPE 720 device with respect to a region of interest of the user. In some exemplary embodiments, the report may provide a color-coded graphical representation of a PPE 720 device virtual fit on the user. In some exemplary embodiments the color-coded graphical representation may illustrate, through color-coding, different levels of pressure as applied to the user by the PPE 720 device when virtually worn.

Figure 8:
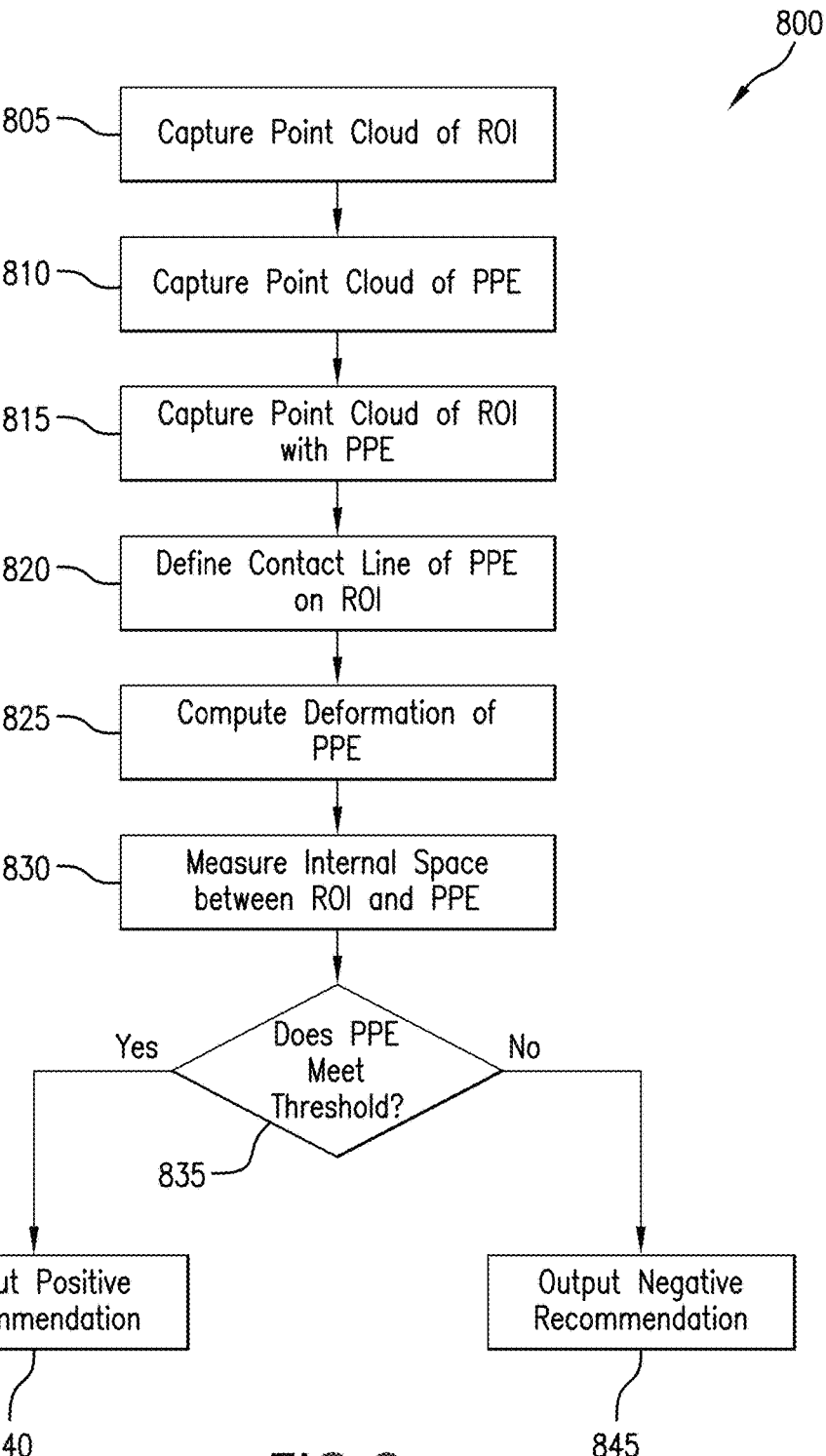
FIG. 8 depicts a flowchart of an exemplary PPE selection system.

FIG. 8 depicts a flowchart of another exemplary PPE selection system. In the exemplary system 800, an optimal fit PPE for a user body part based on an internal space measured between the PPE and the body part. The system provides a method of measuring an internal or hidden space between a PPE and an associated body part to generate an objective fit of the PPE on the body part. For example, a point cloud of an outside part of a PPE may be captured during a deformed and non deformed state to determine a position or shape of an inside part of a PPE. In the depicted example, a point cloud may be captured of a region of interest (ROI) of a body part of the user as in step 805. For example, a point cloud may be captured of a facial area of the user. A point cloud may be captured of a PPE as in step 810, such as for example a respirator. In an exemplary embodiment, a point cloud may be captured both of the outside part (e.g., outside surface) and the inside part (e.g., inside surface) of the PPE. A point cloud may also be captured of the ROI with the PPE being worn as in step 815.

In an exemplary embodiment, the point cloud data may include x, y, z coordinates which may be assembled to form a 3D image of the intended PPE and/or user body part. In an exemplary embodiment, a point cloud may include semantic information or other identifying feature points of the user body part and/or PPE. In some exemplary embodiments, an image capture device may directly capture a 2D or 3D image of the selected body part ROI and/or PPE. In some exemplary embodiments, previously captured 2D or 3D images of body part ROI and/or PPE may be used. In an exemplary embodiment, when there is not a 3D PPE model, captured point cloud of people with and without device may be retrieved independently and compared to get placement information for the outside part of PPE. An estimate of placement and fit of the inside part of PPE may be made, for example.

A contact line may also be defined as in step 820. The contact line may be the point or edge that the PPE makes contact with the user ROI, such as for example a sealing edge of a respirator on a face of a user. Once the contact line is determined a portion of the ROI that is confined or within the contact line may be determined as will be described.

A deformation of the PPE may also be calculated, measured, or determined as in step 825. For example, a deformation of an inside or outside part of the PPE may be calculated or measured based on a deformation of a respective outside or inside part of the PPE. In an exemplary embodiment, a degree of deformation may be predetermined by a manufacturer. In another exemplary embodiment, a degree of deformation may be determined by an employer based on common workplace practices. In an exemplary embodiment, the inside or outside part of the PPE may be used to generate the deformed PPE structure, thus only one of the inside or the outside part of the PPE may be needed.

The internal space between the PPE and the portion of the ROI confined by the contact line may then be measured as in step 830. In an exemplary embodiment, the internal space may be determined based on a perpendicular distance between the PPE and the ROI. In another exemplary embodiment, the internal space may be determined by a contained volume between the PPE and the ROI. In an exemplary embodiment, the internal space may be measured while the PPE is in a deformed state.

A comparator module may determine whether a threshold has been met by the measured internal space as in step 835. If a predetermined threshold has been met, then a positive recommendation may be outputted to a user as in step 840. In an exemplary embodiment, a 3D visual representation of the PPE on the ROI may be displayed to the user. In another exemplary embodiment, the internal measurement may be displayed on the 3D visual representation. If a predetermined threshold has not been met, then a negative recommendation may be outputted to a user as in step 845. For example, if the distance between an internal surface of a respirator and the beneath facial area does not meet a predetermined length, then the respirator may fail a fit test.

Figure 9A:
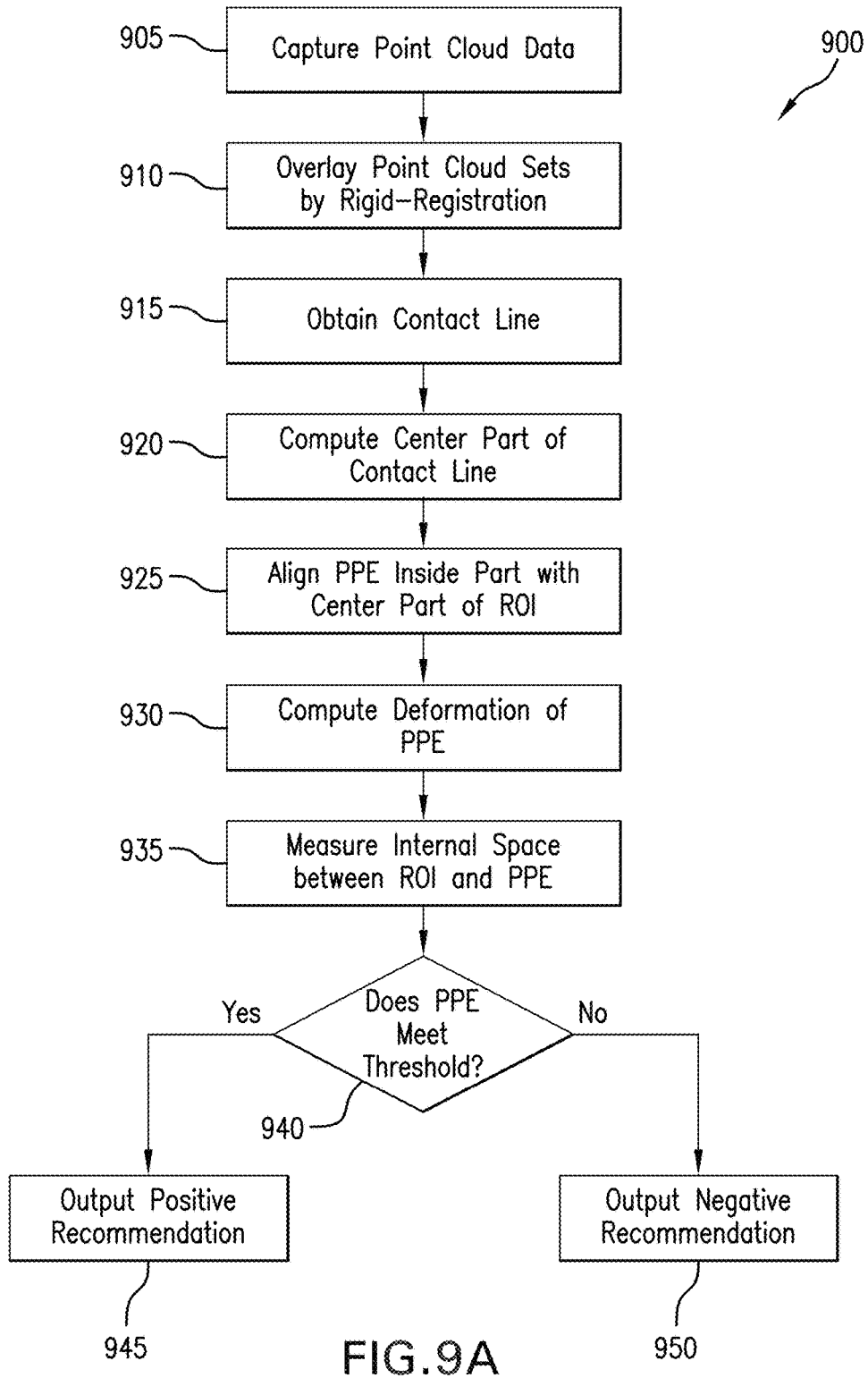
FIG. 9A depicts a flowchart of another exemplary PPE selection system.

FIG. 9A depicts a flowchart of another exemplary PPE selection system. In the exemplary system 900, an optimal fit PPE for a user body part based on an internal space measured between the PPE and the body part. In the depicted example, the system 900 may compute a fit of the PPE on the user body part based on previously captured point clouds of the PPE and/or body part. In an exemplary embodiment, point cloud data may be captured of the body part ROI (e.g., face) and the PPE (e.g., respirator) as in step 905. In some exemplary embodiments, point cloud data may be captured of the ROI with the PPE being worn.

If the PPE is not presently available, previously captured and stored point cloud data may be used to determine placement of the PPE on the ROI. For example, point cloud data of the PPE may be overlaid upon point cloud data of the ROI as in step 910. In an exemplary embodiment, the point cloud data may be aligned using a rigid-registration method. In an exemplary embodiment, the rigid-registration method aligns feature points of the PPE and ROI. In another exemplary embodiment, the rigid-registration method aligns semantic information of the PPE and ROI. In another exemplary embodiment, the rigid-registration method aligns corresponding vertices of the PPE and ROI.

In an exemplary embodiment, once the PPE is placed on the ROI, a contact line of the PPE on the ROI may be obtained as in step 915. The contact line may be the point or edge that the PPE makes contact with the user ROI, such as for example a sealing edge of a respirator on a face of a user.

In an exemplary embodiment, the contact line may be visibly or computationally defined and such that a center part of the contact line may be determined. For example, the center part of the contact line may be the center of a medial axis of the contact line. In an exemplary embodiment, the medial axis may be vertically oriented and separate left and right sides of the space confined by the contact line. A center part of an inside part of the PPE may also be computationally determined and the center part of the PPE and the center part of the ROI are aligned. In an exemplary embodiment, rigid-registration methods may be used to obtain placement of the PPE on the ROI by aligning the center parts of the PPE and the ROI. Once the center parts of the ROI and PPE are aligned, corresponding points of the ROI and PPE may be determined and confirmed such as for making internal measurements.

A deformation of the PPE may be calculated, measured, or determined as in step 930. For example, a deformation of an inside or outside part of the PPE may be calculated or measured based on a deformation of a respective outside or inside part of the PPE. In an exemplary embodiment, a degree of deformation may be predetermined by a manufacturer. In another exemplary embodiment, a degree of deformation may be determined by an employer based on common workplace practices. In an exemplary embodiment, the inside or outside part of the PPE may be used to generate the deformed PPE structure, thus only one of the inside or the outside part of the PPE may be needed.

The internal space between the PPE and the portion of the ROI confined by the contact line may then be measured as in step 935. In an exemplary embodiment, the internal space may be determined based on a perpendicular distance between the PPE and the ROI. In another exemplary embodiment, the internal space may be determined by a contained volume between the PPE and the ROI. In an exemplary embodiment, the internal space may be measured while the PPE is in a deformed state.

A comparator module may determine whether a threshold has been met by the measured internal space as in step 940. If a predetermined threshold has been met, then a positive recommendation may be outputted to a user as in step 945. In an exemplary embodiment, a 3D visual representation of the PPE on the ROI may be displayed to the user. In another exemplary embodiment, the internal measurement may be displayed on the 3D visual representation. If a predetermined threshold has not been met, then a negative recommendation may be outputted to a user as in step 950. For example, if the distance between an internal surface of a respirator and the beneath facial area does not meet a predetermined length, then the respirator may fail a fit test.

Figure 9B:
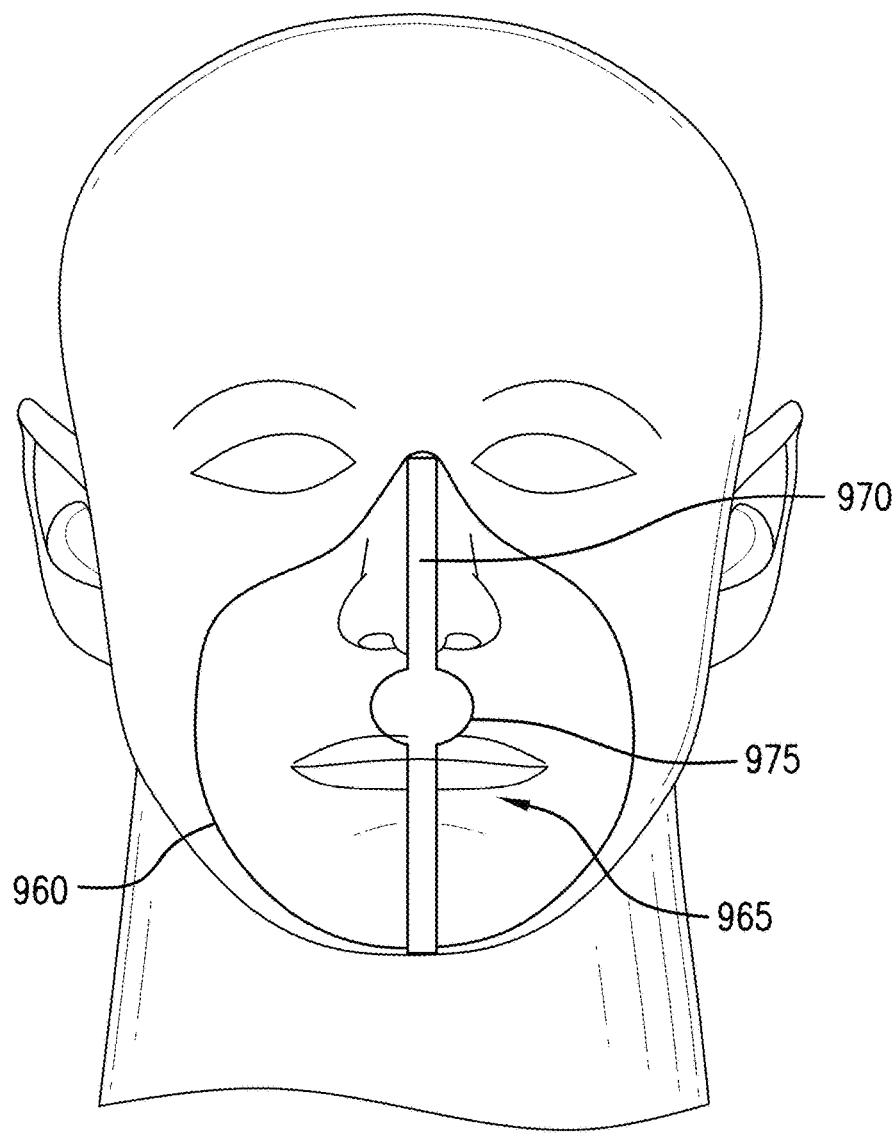
FIG. 9B depicts an exemplary center part on a ROI as defined with reference to FIG. 9A.

FIG. 9B depicts an exemplary center part on a ROI as defined with reference to FIG. 9A. A region of interest ROI 955 may be a body part that is to be protected, such as by a corresponding PPE. In an exemplary embodiment, the ROI 955 may be a facial area of a user. The ROI 955 may be illustrated in a 3D form to a user. In an exemplary embodiment, the ROI 955 includes point cloud data used in the construction of the 3D form and the fitting of the PPE.

In an exemplary embodiment, a contact line 960 may be defined on the ROI 955, as previously defined with reference to step 915 of FIG. 9A. The contact line 960 may be peripheral edge of the PPE that makes contact with the ROI 955, such as for example a sealing edge of a respirator. In an exemplary embodiment, the contact line 960 may be computationally determined by comparing a user ROI while wearing and while not wearing a PPE. In another exemplary embodiment, the contact line 960 may be manually drawn on the ROI by tracing a peripheral edge of the PPE worn on the ROI.

A center part 965 of the contact line 960 may also be defined, as previously defined with reference to step 920 of FIG. 9A. In an exemplary embodiment, the center part 965 includes a medial axis 970 and axis center 975. The medial axis 970 may separate two-halves of the area of the ROI 955 defined by the contact line 960. For example, the medial axis 970 may separate left and right halves of the area of the ROI 955 defined by the contact line 960. In an exemplary embodiment, the axis center 975 may be the lengthwise center of the medial axis 970.

In an exemplary embodiment, a PPE center part including a PPE medial axis and PPE axis center are also defined on the PPE with reference to a contact edge (e.g., sealing edge of a respirator). The PPE medial axis and PPE axis center of the PPE are then aligned with the medial axis 970 and axis center 975 of the ROI to determine a placement of the PPE on the ROI, as previously defined with reference to step 925 of FIG. 9A.

Figure 10:
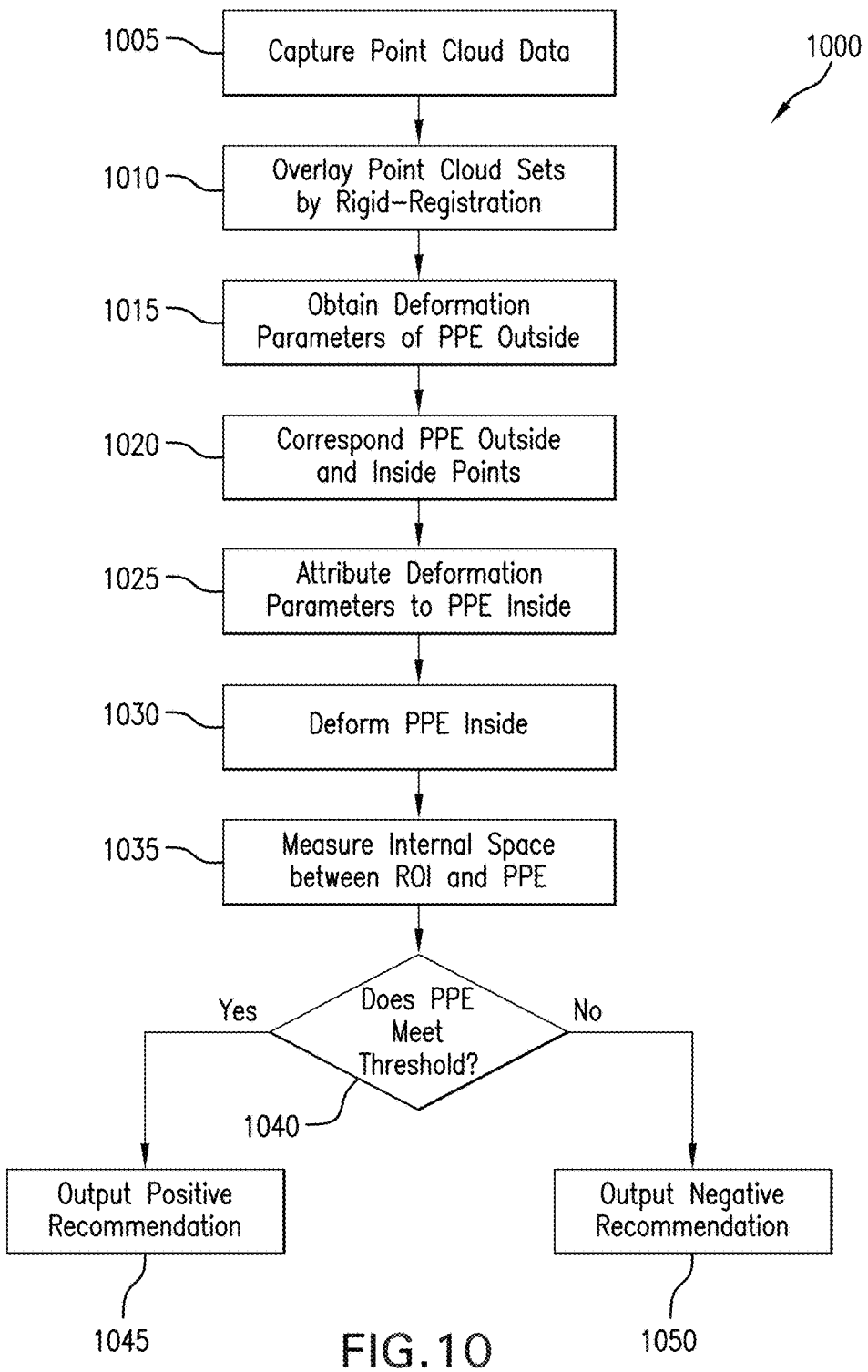
FIG. 10 depicts a flowchart of an exemplary deformation process.

FIG. 10 depicts a flowchart of an exemplary deformation process. A deformation module 1000 may determine a deformation of an inside part of PPE by correspondence with a deformation of an outside part of the PPE to obtain an internal measurement of the PPE and body part for determining whether the PPE fits the body part. The module 1000 first captures point cloud data of the body part and PPE as in step 1005. In some exemplary embodiments, the point cloud data may be captured earlier in the process and relayed to the deformation module 1000. The point cloud sets are overlaid upon each other as in step 1010 to fit the PPE to the body part. In some exemplary embodiments, the fitting process may be performed by other modules and the result relayed to the deformation module 1000.

The module 1000 may then obtain deformation parameters of the outside part of the PPE as in step 1015. In an exemplary embodiment, the outside part of the PPE may be an outside surface of the PPE with respect to the PPE being worn by a user. In an exemplary embodiment, the deformation parameters may be predetermined according to specific construction properties of the PPE. In another exemplary embodiment, the deformation parameters may be determined by functions, such as for example the deformation function described with reference to FIG. 6A.

The PPE outside part may then be corresponded to the PPE inside part as in step 1020. For example, corresponding inside and outside part points may be correlated based upon a nearest distance between inside points and outside mesh nodes. In another exemplary embodiment, inside points or vertices determined to be physically affected by specific outside points or vertices are linked. For example, moving a point A on an outside part may correspondingly move a point B on an inside part of the PPE, and thus point A may be linked to some degree to point B.

Once all necessary inside and outside part points of the PPE have been linked, the outside point deformation parameters previously defined in step 1015 are attributed to the respective inside points as in step 1025. The PPE inside part may then be computationally deformed as in step 1030. In an exemplary embodiment, the PPE inside part may be deformed according to the attributed deformation parameters linked to the respective inside part in step 1025.

The internal space between the inside part of the PPE and the portion of the ROI confined by the contact line may then be measured as in step 1035. In an exemplary embodiment, the internal space may be measured while the inside part of the PPE is in the deformed state. In an exemplary embodiment, the internal space may be determined based on a perpendicular distance between the PPE and the ROI. In another exemplary embodiment, the internal space may be determined by a contained volume between the PPE and the ROI.

A comparator module may determine whether a threshold has been met by the measured internal space as in step 1040. If a predetermined threshold has been met a positive recommendation may be outputted to a user as in step 1045. In an exemplary embodiment, a 3D visual representation of the PPE on the ROI may be displayed to the user. In another exemplary embodiment, the internal measurement may be displayed on the 3D visual representation. If a predetermined threshold has not been met, then a negative recommendation may be outputted to a user as in step 1050. For example, if the distance between an internal surface of a respirator and the beneath facial area does not meet a predetermined length, then the respirator may fail a fit test.

Figure 11:
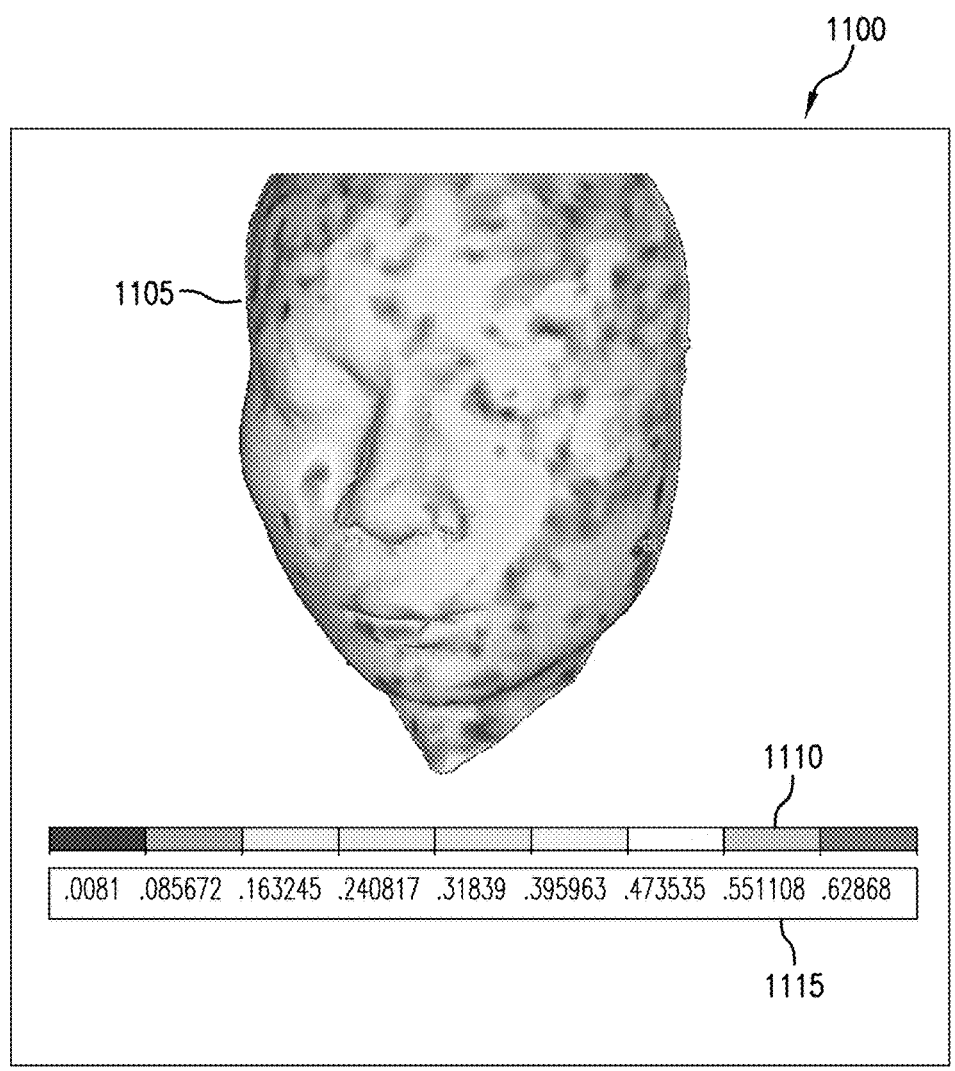
FIG. 11 depicts a graphical representation of an exemplary color-coded display of a PPE fit.

FIG. 11 depicts a graphical representation of an exemplary color-coded display of a PPE fit. A display 1100 may be outputted to a user by an output module for providing a visual recommendation of a PPE fit. In an exemplary embodiment, the display 1100 may be outputted on a computer screen. In another exemplary embodiment, the display 1100 may be outputted in a printable format.

The display 1100 includes a representation of the evaluated user body part 1105, for example a facial area. In an exemplary embodiment, the body part 1105 may be portrayed in 3D form. The body part 1105 may be colored according to pressure distribution as applied on the body part 1105 by the PPE. In an exemplary embodiment, the PPE may be shown with the body part 1105. In the depicted example, the display 1100 includes a reference chart 1110 of the colors illustrated on the body part 1105 and values 1115 associated with each of the colors on the color chart 1110. The values 1115 may represent ranges of pressure distribution, for example.

In an exemplary embodiment, a user may visually determine whether a PPE would provide an acceptable fit by visualizing whether any areas upon the body part 1105 are a certain color. For example, if an area of the body part 1105 were colored red, a high degree of applied pressure may be applied to the body part 1105 by the respective PPE. For example, a respirator may fit tightly against a face of a user in a certain area. In an exemplary embodiment, if a certain color were displayed on the body part 1105 which would represent a threshold being exceeded, the respective PPE may be disqualified from further consideration with respect to the specific user.

In another exemplary embodiment, shapes or symbols, rather than colors may be visually displayed on the body part 1105 to symbolize measured criteria. For example, a first shape may represent a first pressure applied to the body part 1105 by the PPE and a second color may represent a second pressure applied to the body part 1105 by the PPE. In another exemplary embodiment, a first color, shape, or pattern may be overlaid upon the body part 1105 to represent a first distance that the PPE is from the body part when virtually worn, and a second color, shape, or pattern may be overlaid upon the body part 1105 to represent a second distance that the PPE is from the body part when virtually worn.

Figure 12:
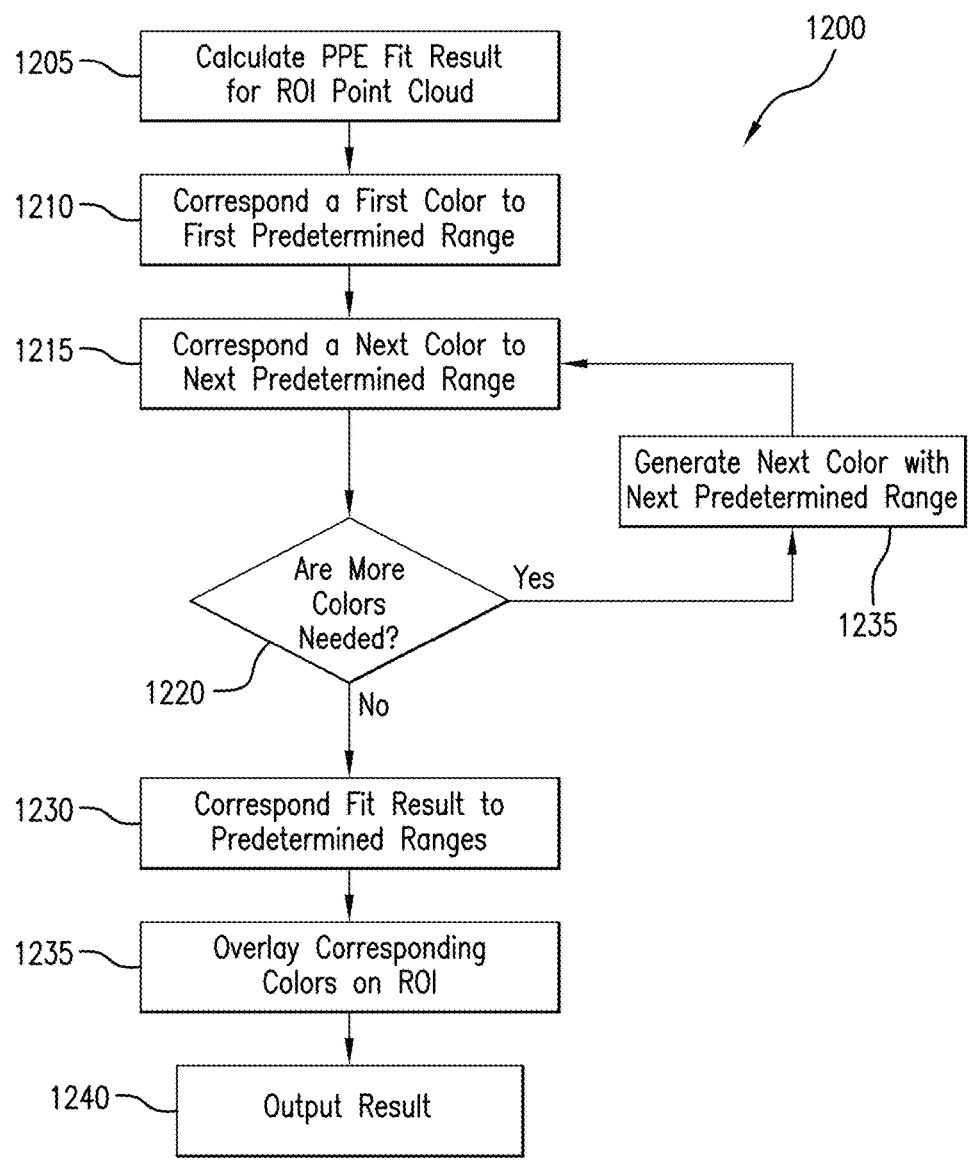
FIG. 12 depicts a flowchart of an exemplary color-coded result generator.

FIG. 12 depicts a flowchart of an exemplary color-coded result generator. A color-coded result generator 1200 may associated a set of fit results with one or more colors to provide a user with a quick method of determining whether a respective PPE would fit and/or be comfortable. The fit results may be calculated and assigned to each of the points on the point cloud, such that each point in the point cloud of the ROI may have an associated fit result as illustrated in step 1205. The result generator 1200 may calculate and assign the fit results or the fit results may be imported. In an exemplary embodiment, the fit results each include an applied pressure upon the body part by the PPE. For example, the fit results may include a pressure applied to a facial area by the respirator at each defined point or vertices.

The generator 1200 may correlate one or more colors to one or more predetermined ranges as in steps 1210 and 1215. For example, a first range of applied pressure values may be assigned a first color, for example a blue color. A second range of applied pressure values may be assigned a second color, for example a green color. The generator determines whether more colors are needed as in step 1220 and generates additional colors with assigned predetermined ranges as in step 1225. In another exemplary embodiment, a set of predetermined colors may be initially assigned that include all possible ranges, such as for example from $-\infty$ to $+\infty$.

The color ranges may then be corresponded to the fit results as in step 1230. For example, a green color overlay on the human body part may represent an optimal match and a red color overlay on the human body part may represent a non optimal match. In an exemplar embodiment, the colors may represent how tight or loose PPE may be relative the human body part, such as for example red being shown for an area of the body part where the PPE product fits too tightly and green may be shown for an area of the body part where the PPE product fits too loosely.

The colors may then be overlaid on a body part ROI representation as in step 1235 and the result may be outputted to the user as in step 1240. In an exemplary embodiment, the body part ROI representation may be in 3D form. An exemplary output is shown by display 1100 of FIG. 11.

Although various embodiments have been described with reference to the Figures, other embodiments are possible. For example, in some embodiments, the system and method for automatically selecting a respirator may comprise predictive software that may capture a facial image and match the facial image to the closest form of a respirator model, type, and/or size. In an exemplary embodiment, the software may use a dynamic set of images and match the images to the flexibility of a respirator shape to predict an interface between the respirator model and the facial model. For example, the software may predict whether the interface between the respirator and the facial area will result in separation thus permitting leakage or breach in the sealing surface.

In various embodiments, the image capture device may be a 3D digital scanner, such as for example one or more Kinect devices manufactured by Microsoft®. In some embodiments, the image capture device may be a still camera device. In some exemplary embodiments, the image capture device may be a video recorder device. In some exemplary embodiments, the image capture device may be a handheld unit. The image capture device may be wirelessly connected to a processing module for receiving a scanned image from the image capture device and determining whether a scanned or modeled PPE fits a scanned or modeled body part. In some exemplary embodiments, the image capture device may be a low-cost item.

In various embodiments, apparatus and methods may involve a digital image of a facial area of a user in a variety of facial positions. For example, a first facial position may be a grin or smile. A second facial position may be the user voicing specific letters and/or sounds. In an exemplary embodiment, software may digitize the facial shape of the user in each of the facial positions to create a flexible electronic file, for example. In an exemplary embodiment, software may also store files having contours of respirators in both a static state and in a flexed state for comparison to facial shape files. In an exemplary embodiment, the software may match up a negative cavity of the respirator model with a positive face form of the facial area model to determine a fit level of a respirator or best fit respirator. In some exemplary embodiments, software may match the respirator and the facial area in both static and dynamic positions of the facial area and/or respirator to determine whether a respirator will fit in a variety of facial positions and/or flexed positions of the respirator.

In an exemplary embodiment, an administrator may oversee a matching process of the respirator and a specific facial area. For example, an administrator at a workplace may oversee the matching process for each new employee. In some examples, each employee may undergo a matching process, such as for example via a pay per use web link. In some exemplary embodiments, a kiosk or vending machine may include software functionality to perform a matching process between one or more respirators and a specific facial shape. For example, a user may scan a user facial shape at a kiosk, and the kiosk may geometrically compare the facial shape of the user to a plurality of respirator models available for dispensing to find a respirator that most closely matches the facial shape of the user. Upon finding an optimal or best fit respirator, the kiosk may dispense the respective respirator or provide direction to the user on where the respirator may be available for pickup and/or purchase, for example.

In accordance with another embodiment, a population data gathering and storage system may be made available via scanning facial areas of users. In some examples, the facial shapes gathered and stored via the matching process may be used by respirator manufacturers to improve a respirator design such that newly manufactured respirators more closely match a common facial shape of persons commonly wearing the respirators. In some examples, the facial shapes gathered and stored via the matching process may be used by employers to provide insight on which respirators to stock in greater or less numbers. In some exemplary embodiments, a captured point cloud of a PPE and/or a user body part may be re-used in other PPE design.

In accordance with another embodiment, a variety of body parts may be scanned and captured for being matched with respective clothing or garments. For example, a hand of a user may be scanned and stored as a data set such that a variety of glove models, types, and/or sizes may be compared against the hand of the user to find an optimal or best fit glove. In another exemplary embodiment, a head of a user may be scanned and stored as a data set such that a variety of helmet models, types, and/or sizes may be compared against the head of the user to find an optimal or best fit helmet.

In accordance with an exemplary embodiment, a system and method for selecting a respirator may include a body modeling module for capturing an image(s) of a body part (e.g., facial area) of a user. In an exemplary embodiment, the image(s) may be used to generate a 3D model of the body part.

In some embodiments, the system and method for selecting a respirator may include one or more product databases of PPE 3D models. For example, each product database may include PPE to be worn on a specific body part. In an exemplary embodiment, a respirator database may be associated with facial areas, a glove database may be associated with hands, and a helmet database may be associated with heads. In some exemplary embodiments, the material properties of each specific PPE may also be stored with the specific PPE model.

In some embodiments, the system and method for selecting a respirator may include a rule library illustrating a method of mapping 3D PPE models to a 3D human body part. In an exemplary embodiment, a rule library may include three types of rules, such as for example association rules, mapping rules, and evaluation rules. For example, association rules may define which related PPE 3D models from the product database are associated to a target body part. For example, respiratory products from product database may be associated to face models, and footwear products from product databases may be associated to foot models. In an exemplary embodiment, mapping rules may define how the product model will be mounted to the body model, such as for example by mapping directions, forces, and/or deformations according to a material property. In an exemplary embodiment, evaluation rules may define how well the PPE fits the body part in accordance with a mapping result. For example, via dimensional comparison, a body dimension may be compared to a related product dimension range or pressure distribution during and after the product is mapped to the body part.

In some embodiments, the system and method for selecting a respirator may include a 3D geometry matching module. In an exemplary embodiment, the matching module may calculate all differences between the 3D PPE models and the 3D human body model. The geometry matching module may select a PPE part according to association rules, determine the difference with the mapping rules, summarize the difference according to the evaluation rules, and then propose a product model and/or size which may optimally fit a user. In an exemplary embodiment, a top three or top five best fitting products may be provided to the user.

In some embodiments, the system and method for selecting a respirator may include a simulator module. In an exemplary embodiment, a simulator module may visualize to a user how well the PPE model fits on the body part model. In some exemplary embodiments, the simulator may display the human body part and PPE product in 3D representations. In some exemplary embodiments, color coding may be used to illustrate how well the PPE fits a human body part. For example, a green color overlay on the human body part model may represent an optimal match and a red color overlay on the human body part model may represent a non optimal match. In some examples, the colors may represent how tight or loose the PPE may be relative the human body part, such as for example red being shown on an area of the body part model where the PPE fits too tightly and green shown on an area of the body part model where the PPE fits too loosely.

In accordance with an exemplary embodiment, the PPE selection system may output a comfort level based on a predetermined measurement scale, where the comfort level may reference a relative comfort of a PPE virtually worn by a user. In some embodiments, a comfort level may be determined by the amount of internal space measured between an inside part of a PPE and a corresponding body part. In some exemplary embodiments, a comfort level may be determined by a degree of permissible movement by a respective body part while a PPE is worn. For example, a comfort level may be determined for a respirator by determining whether the respirator maintains a seal with a facial area while the mouth of the user is being opened. In accordance with an exemplary embodiment, a user feeling may be determined by an objective comfort evaluation based on quantitative measurement. For example, a module may calculate a numeric pressure level upon the facial model as applied by the respirator model and compare the calculated pressure level with a set of predetermined pressure ranges each associated with a specific comfort level.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were supplemented with other components. Accordingly, other implementations are within the scope of the following claims.

What is claimed is:

1. A method of predictively fitting a respirator to a specific user, the method comprising:
retrieving respirator shape data representative of a shape of a selected respirator;
capturing facial shape data representative of a facial shape of a selected facial area;
overlaying said respirator shape data upon said facial shape data to obtain deformation parameters for said respirator;
computationally deforming the respirator shape data according to the obtained deformation parameters;
determining an internal dimension between an internal surface of said respirator and a portion of said facial area behind said respirator;
generating a fit recommendation for display to a user based upon said internal dimension between said respirator and said facial area; and,
generating a color-coded display of said facial area indicative of a degree of fit of said respirator on said facial area.

2. The method of claim 1, further comprising a step of determining whether said internal dimension exceeds a minimum threshold, wherein said fit recommendation is based on said minimum threshold.

3. The method of claim 1, wherein said internal dimension comprises a distance between said respirator and said facial area.

4. The method of claim 1, wherein said internal dimension comprises an internal volume between said respirator and said facial area.

5. The method of claim 1, further comprising a step of computing an internal shape of said respirator based upon an external shape of said respirator.

6. The method of claim 1, further comprising a step of overlaying said respirator upon said facial area in a deformed state of said respirator.

7. The method of claim 1, further comprising a step of overlaying said respirator upon said facial area in a non-deformed state of said respirator.

8. The method of claim 1, further comprising a step of storing a plurality of point cloud data sets each representative of a shape and size of a specific respirator in a respirator database.

9. A method of predictively fitting a respirator to a specific user, the method comprising:
retrieving respirator shape data representative of a shape of a selected respirator;
capturing facial shape data representative of a facial shape of a facial area of a user, wherein said facial shape data is captured with and without said respirator being worn;
overlaying said respirator shape data upon said facial shape data to obtain deformation parameters for said respirator;
computationally deforming the respirator shape data according to the obtained deformation parameters;
determining a contact line of said respirator on said facial area for location of a portion of said facial area behind said respirator;
determining an internal dimension between an internal surface of said respirator and said portion of said facial area behind said respirator;
generating a fit recommendation for display to a user based upon said internal dimension between said respirator and said facial area, and,
generating a color-coded display of said facial area indicative of a degree of fit of said respirator on said facial area.

10. The method of claim 9, further comprising a step of determining whether said internal dimension exceeds a minimum threshold, wherein said fit recommendation is based on said minimum threshold.

11. The method of claim 9, wherein said internal dimension comprises a distance between said respirator and said facial area.

12. The method of claim 9, wherein said internal dimension comprises an internal volume between said respirator and said facial area.

13. The method of claim 9, further comprising a step of computing an internal shape of said respirator based upon an external shape of said respirator.

14. The method of claim 9, further comprising a step of modifying said respirator shape data to a deformed state.

15. The method of claim 9, further comprising a step of overlaying said respirator upon said facial area in a non-deformed state of said respirator.

16. A system for predictively fitting a respirator to a specific user, the system comprising:

a processor module for defining facial shape data corresponding to a facial shape of a facial area and respirator shape data corresponding to a respirator shape and size;

means for determining an internal dimension between said respirator and said facial area by overlaying said respirator shape data upon said facial shape data to obtain deformation parameters for said respirator and computationally deforming the respirator shape data according to the obtained deformation parameters; and, a recommendation module for display to a user based upon said internal dimension, wherein said recommendation module comprises a color-coded facial area display configured to display a color-coded display of said facial area indicative of a degree of fit of said respirator on said facial area.

17. The system of claim 16, wherein said processing module computes an internal shape of said respirator based upon an external shape of said respirator.

* * * * *